US007124635B2

(12) United States Patent
Kushibiki et al.

(10) Patent No.: US 7,124,635 B2
(45) Date of Patent: Oct. 24, 2006

(54) EVALUATION METHOD FOR COEFFICIENT OF THERMAL EXPANSION OF ULTRA-LOW-EXPANSION GLASS MATERIAL

(75) Inventors: Jun-ichi Kushibiki, Miyagi (JP);
Mototaka Arakawa, Miyagi (JP); Yuji Ohashi, Miyagi (JP); Yukihiro Shinozaki, Tokyo (JP)

(73) Assignees: Tohoku University, Miyagi (JP); Chuo Precision Industrial Co., Ltd., Tokyo (JP)

( * ) Notice: Subject to any disclaimer, the term of this patent is extended or adjusted under 35 U.S.C. 154(b) by 0 days.

(21) Appl. No.: 11/195,945

(22) Filed: Aug. 2, 2005

(65) Prior Publication Data
US 2006/0028096 A1    Feb. 9, 2006

(30) Foreign Application Priority Data
Aug. 6, 2004    (JP)    ............... 2004-231023

(51) Int. Cl.
*G01N 29/04*    (2006.01)
(52) U.S. Cl. .......................................... 73/602; 73/606
(58) Field of Classification Search ................. 73/602, 73/606
See application file for complete search history.

(56) References Cited

U.S. PATENT DOCUMENTS

| 5,211,059 A | * | 5/1993 | Hayakawa et al. | ............ 73/606 |
| 5,349,862 A | * | 9/1994 | Chubachi et al. | ............ 73/602 |
| 2002/0124651 A1 | * | 9/2002 | Kushibiki et al. | ............ 73/579 |

FOREIGN PATENT DOCUMENTS

| JP | 59206758 A | * | 11/1984 |
| JP | 06058915 A | * | 3/1994 |
| JP | 09072889 A | * | 3/1997 |
| JP | 2002-257502 | | 9/2002 |

OTHER PUBLICATIONS

Hrdina, K., et al., "Measuring and tailoring CTE within ULE Glass," Proc. SPIE, Emerging Lithographic Technologies VII, vol. 5037, pp. 227-235 (2003).
Mitra, I., et al., "Thermal expansion behavior of proposed EUVL substrate materials," Proc. SPIE, vol. 4688, pp. 462-468 (2002).
Hagy, H., et al., "Determining absolute thermal expansion of titania-silica glasses: a refined ultrasonic method," Appl. Opt., vol. 14, pp. 2099-2103 (1975).

(Continued)

Primary Examiner—Hezron Williams
Assistant Examiner—Rose M. Miller
(74) Attorney, Agent, or Firm—David N. Lathrop, Esq.; Gallagher & Lathrop

(57) ABSTRACT

By measuring, for an ultra-low-expansion glass material, the frequency dependence of acoustic velocities and attenuation coefficients of bulk waves (longitudinal waves and shear waves), and the density, its fundamental acoustic properties are revealed, and a standard specimen for use in system calibration is prepared. By an absolute calibration method using the standard specimen, absolute values for both the LSAW and LSSCW velocities are obtained. Moreover, there are obtained relationships for the acoustic properties and the coefficient of thermal expansion to evaluate the coefficient of thermal expansion from the acoustic properties. In case there is a distribution of characteristics due to periodic striae, an accurate acoustic property distribution in the substrate can be ascertained and an evaluation performed, by selecting for the substrate a cutting angle with respect to the striae plane.

7 Claims, 30 Drawing Sheets

OTHER PUBLICATIONS

Kushibiki, J., et al., "Development of the line-focus-beam ultrasonic material characterization system," IEEE Trans. Ultrason., Ferrolect., Freq. Contr., vol. 49, pp. 99-113 (2002).

Kushibiki, J., et al., "Material characterization by-line-focus-beam acoustic microscope," IEEE Trans. Sonics and Ultrason., vol. SU-32, pp. 189-212 (1985).

Kroebel, W., "Recent results of absolute sound velocity measurements in pure water and sea water at atmospheric pressure," Acustica, vol. 35, pp. 154-164 (1976).

Kushibiki, J., et al., "A method for calibrating the line-focus-beam acoustic microscopy system," IEEE Trans. Ultrason., Ferrolect. Freq. Contr., vol. 45, pp. 421-430 (1998).

Campbell, J., et al., "Propagation of surface waves at the boundary between a piezoelectric crystal and a fluid medium," IEEE Trans. Sonics Ultrason., vol. SU-17, pp. 71-76 (1970).

Viktrov, I., "Rayleigh and Lamb Waves: Physical Theory and Applications," (Plenum, New York, 1967); Chap. I, pp. 46-57.

Williams, Jr., A., "The piston source at high frequencies," J. Acoust. Soc. Am., vol. 23, pp. 1-6 (1951).

Kushibiki, J., et al., "Precise measurements of bulk-wave ultrasonic velocity dispersion and attenuation in solid materials in the VHF range," J. Acoust. Soc. Am., vol. 113, pp. 3171-3178 (2003).

Arakawa, J., et al., "An evaluation of effective radiuses of bulk-wave ultrasonic transducers as circular piston sources for accurate velocity measurements" IEEE Trans. Ultrason., Ferroelect., Freq. Contr., vol. 51, pp. 496-501 (2004).

Pinkerton, J., "The absorption of ultrasonic waves in liquids and its relation to molecular constitution," Proc. Phys. Soc., vol. B62, pp. 129-141 (1949).

Hashimoto, Y., et al., "Measurements of ultrasonic attenuation coefficients of water in VHF/UHF range," Tech. Rep. IEICE, vol. US97-50, pp. 37-42 (1997).

Kushibiki, J., et al., "High-accuracy standard specimens for the line-focus-beam ultrasonic material characterization system," IEEE Trans. Ultrason., Ferroelect., Freq. Contr., vol. 49, pp. 827-835 (2002).

Gerlich, D., et al., "Thermoelastic properties of Zerodur glass-ceramic," J. Non-Cryst. Solids, vol. 27, pp. 209-214 (1978).

* cited by examiner

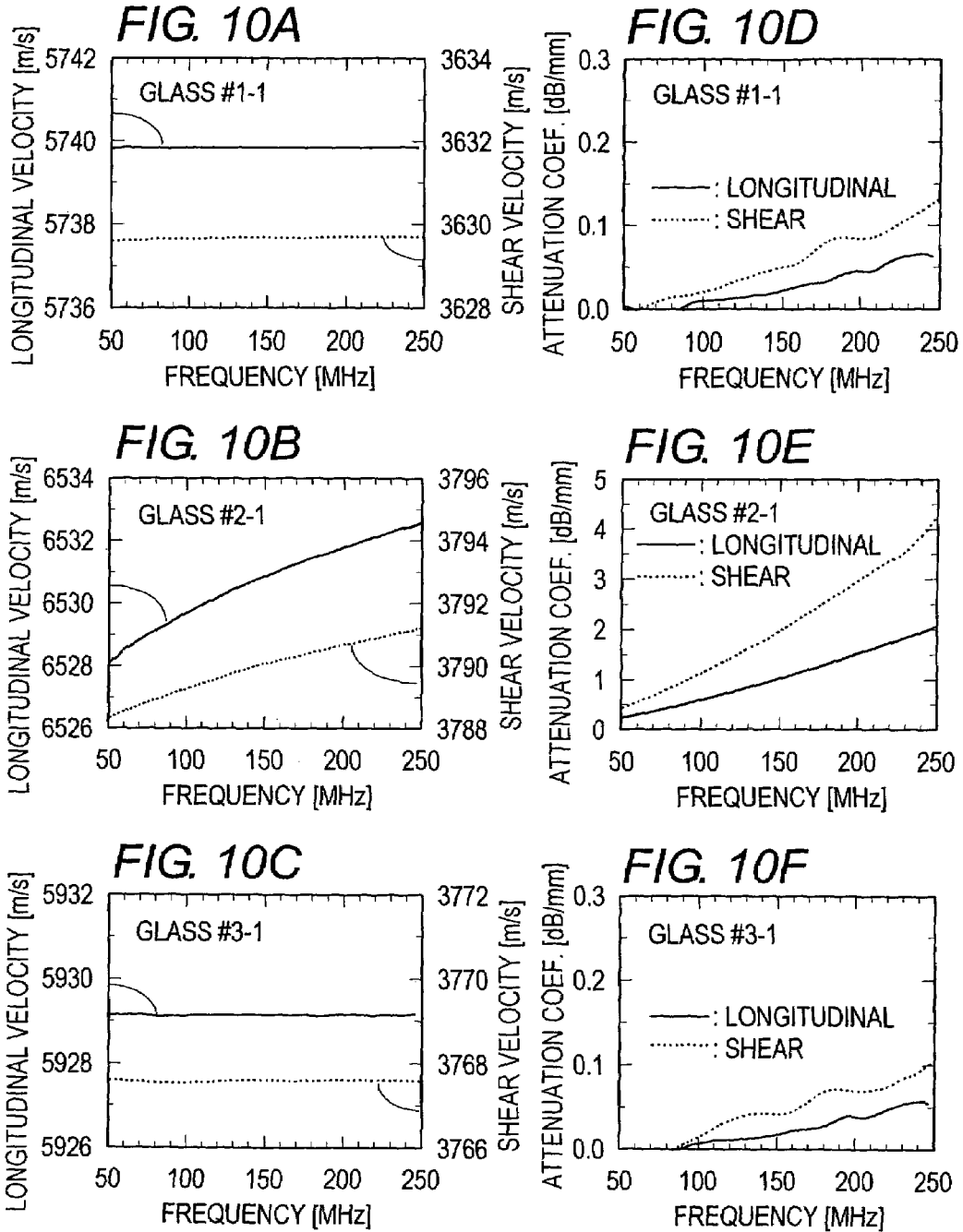

FIG. 14

| SPECIMEN | SiO₂ | Al₂O₃ | P₂O₅ | Li₂O | K₂O | MgO | As₂O₃ | TiO₂ | ZrO₂ | ZnO |
|---|---|---|---|---|---|---|---|---|---|---|
| #1-1 | 93.1 | | | | | | | 6.9 | | |
| #2-1 | 58.3 | 24.2 | 7.1 | 3.7* | 0.5 | 1.2 | 0.2 | 2.2 | 1.2 | 1.3 |
| #3-1 | 100 | | | | | | | | | |

(in wt%)

* NON-PATENT LITERAUTRE 16

FIG. 15

| SPECIMEN | LONGITUDINAL VELOCITY (m/s) | SHEAR VELOCITY (m/s) | DENSITY (kg/m³) | $C_{11}$ ($\times 10^{10}$ N/m²) | $C_{44}$ ($\times 10^{10}$ N/m²) |
|---|---|---|---|---|---|
| #1-1 | 5739.87 | 3629.80 | 2197.82 | 7.2410 | 2.8957 |
| #3-1 | 5929.14 | 3767.62 | 2199.82 | 7.7334 | 3.1226 |
| DIFFERENCE | −189.27 (−3.19%) | −137.82 (−3.66%) | −2.00 (−0.09%) | −0.4924 (−6.37%) | −0.2269 (−7.27%) |

FIG. 16

GLASS #1

|  | SENSITIVITY | RESOLUTION |
| --- | --- | --- |
| LSAW VELOCITY | — | ±0.09 (m/s) |
| CTE | 4.33 (ppb/K)/(m/s) | ±0.38 ppb/K |
| $TiO_2$ CONCENTRATION | -0.057 wt%/(m/s) | ±0.005 wt% |
| DENSITY | 0.0167 (kg/m$^3$)/(m/s) | ±0.0014 (kg/m$^3$) |

FIG. 17

GLASS #1

|  | SENSITIVITY | RESOLUTION |
| --- | --- | --- |
| LSSCW VELOCITY | — | ±1.2 (m/s) |
| CTE | 2.76 (ppb/K)/(m/s) | ±3.4 ppb/K |
| $TiO_2$ CONCENTRATION | -0.037 wt%/(m/s) | ±0.045 wt% |
| DENSITY | 0.0106 (kg/m$^3$)/(m/s) | ±0.013 (kg/m$^3$) |

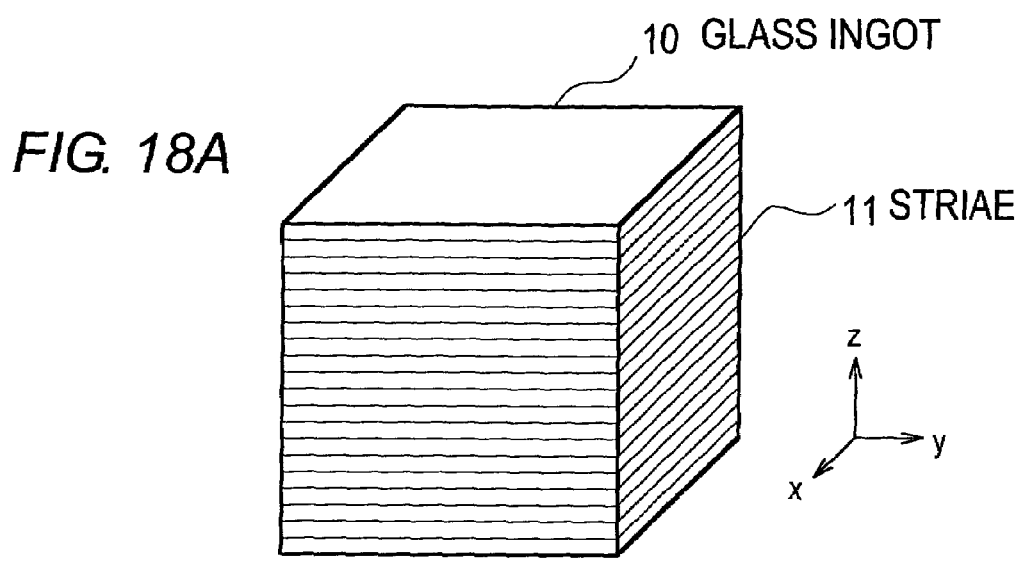
FIG. 18A
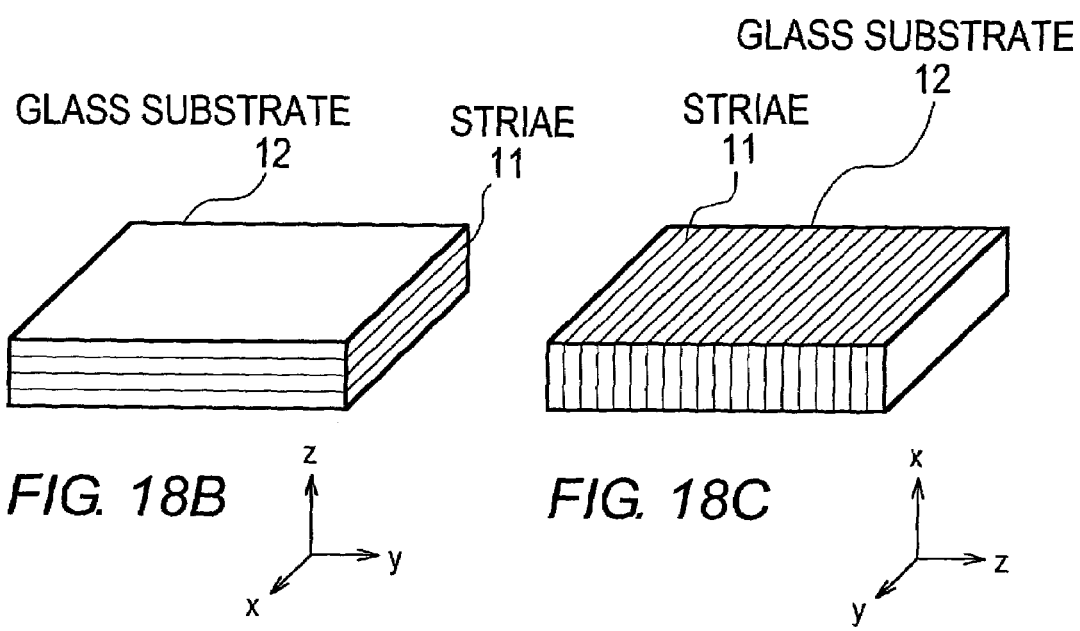
FIG. 18B
FIG. 18C

| SPECIMEN | SiO$_2$ | Al$_2$O$_3$ | K$_2$O | TiO$_2$ | ZrO$_2$ | P$_2$O$_5$ | ZnO | MgO | As$_2$O$_3$ | Li$_2$O* |
|---|---|---|---|---|---|---|---|---|---|---|
| #2-1 | 58.33 | 24.17 | 0.51 | 2.20 | 1.24 | 7.11 | 1.33 | 1.19 | 0.23 | 3.7 |
| #2-2 | 58.37 | 24.32 | 0.51 | 2.17 | 1.24 | 7.05 | 1.30 | 1.19 | 0.16 | 3.7 |
| #2-3 | 58.63 | 24.16 | 0.51 | 2.24 | 1.29 | 6.92 | 1.25 | 1.13 | 0.18 | 3.7 |
| #2-4 | 58.69 | 23.98 | 0.51 | 2.19 | 1.26 | 6.97 | 1.32 | 1.18 | 0.20 | 3.7 |

* NON-PATENT LITERATURE 16

FIG. 26

| SPECIMEN | DENSITY (kg/m$^3$) |
|---|---|
| #2-1 | 2530.75 |
| #2-2 | 2532.83 |
| #2-3 | 2531.02 |
| #2-4 | 2533.10 |

FIG. 30

GLASS #1

|  | SENSITIVITY | RESOLUTION |
|---|---|---|
| LONGITUDINAL VELOCITY | — | ±0.03 (m/s) |
| CTE | 2.75 (ppb/K)/(m/s) | ±0.07 ppb/K |
| $TiO_2$ CONCENTRATION | -0.037 wt%/(m/s) | ±0.0009 wt% |
| DENSITY | 0.0106 (kg/m$^3$)/(m/s) | ±0.0003 (kg/m$^3$) |

FIG. 31

| | LSAW VELOCITY | | | LSSCW VELOCITY | | LONGITUDINAL VELOCITY | | |
|---|---|---|---|---|---|---|---|---|
| | SENSITIV. | RES. (225 MHz) | RES. (75 MHz) | SENSITIV. | RES. | SENSITIV. | RES. (4.8 mm†) | RES. (6.35 mm†) |
| VELOCITY | — | ±0.09 (m/s) | ±0.03 (m/s) | — | ±1.2 (m/s) | — | ±0.03 (m/s) | ±0.02 (m/s) |
| CTE | 4.33 (ppb/K)/(m/s) | ±0.38 ppb/K | ±0.14 ppb/K | 2.76 (ppb/K)/(m/s) | ±3.4 ppb/K | 2.75 (ppb/K)/(m/s) | ±0.07 ppb/K | ±0.06 ppb/K |
| TiO₂ CONC. | -0.057 wt%/(m/s) | ±0.005 wt% | ±0.0019 wt% | -0.037 wt%/(m/s) | ±0.045 wt% | -0.037 wt%/(m/s) | ±0.0009 wt% | ±0.0008 wt% |
| DENSITY | 0.0167 (kg/m³)/(m/s) | ±0.0014 (kg/m³) | ±0.0005 (kg/m³) | 0.0106 (kg/m³)/(m/s) | ±0.013 (kg/m³) | 0.0106 (kg/m³)/(m/s) | ±0.0003 (kg/m³) | ±0.0002 (kg/m³) |

EVALUATION METHOD FOR COEFFICIENT OF THERMAL EXPANSION OF ULTRA-LOW-EXPANSION GLASS MATERIAL

TECHNICAL FIELD

This invention pertains to an evaluation method for a coefficient of thermal expansion of an ultra-low-expansion glass material using the propagation characteristics of leaky acoustic waves, in particular phase velocity, measured by means of an ultrasonic material characterization system.

BACKGROUND ART

At present, the development of generation-after-next Extreme Ultraviolet Lithography (EUVL) is being conducted. As elemental technologies for EUVL systems, the five items of EUV light sources, aspherical optical systems, exposure apparatuses, multilayered photomasks, and photoresist processes can be cited, and the development of those technologies is being conducted in parallel. The most essential and important issue in this development of EUVL systems is to develop ultra-low-expansion glasses as the basic substrate material suitable for optical systems and photomasks. At the same time, measurement and evaluation technologies for accurately ascertaining and analyzing the materials characteristics are vital to the development of those materials.

In EUVL systems, thermal stability in the sub-nanometer range is required for optical lens materials and photomask substrate materials. Specifically, ultra-low-expansion glasses having coefficients of thermal expansion (CTE) not exceeding ±5 ppb/K at the desired temperature (e.g. 22±3° C. in the photomask substrate) become necessary (Non-Patent Reference 1). Here, if the length of a solid at 0° C. is taken to be $L_0$ and the length at a temperature T° C. is taken to be L, the coefficient of thermal expansion is given as $(dL/dT)/L_0$. At present, two types of $TiO_2$—$SiO_2$ glass and $Li_2O$—$Al_2O_3$—$SiO_2$ crystallized glass can be cited as commercially available ultra-low-expansion glasses and are used conventionally as materials for lenses for large astronomical telescopes and semiconductor manufacturing apparatuses (steppers). The former glass realizes an ultra-low expansion coefficient by an adjustment of the ratio of $SiO_2$ and $TiO_2$, and the latter glass realizes it by an adjustment of the crystallization process (annealing temperature and time) in addition to that of the chemical composition ratio (Non-Patent Reference 1 and Non-Patent Reference 2). Even with the best grade among these glasses, the specification for the coefficient of thermal expansion stands at ±20 ppb/K (distribution in a glass ingot; ±10 ppb/K), which is insufficient for the specification for ultra-low-expansion glass for EUVL systems of within ±5 ppb/K at the desired temperature. Recently, manufacturing companies in Japan and other countries have started to carry out trial manufacture of EUVL-grade ultra-low-expansion glasses. For the development of those materials, a measurement accuracy of ±0.2 ppb/K (±σ, σ being the standard deviation) or less with respect to the coefficient of thermal expansion is required (Non-Patent Reference 1).

At present, a number of methods are proposed as methods of evaluating coefficients of thermal expansion of substrates for EUVL use. As a method of directly measuring coefficients of thermal expansion, there is the method of using a dilatometer or the like. These days, products using a laser have been developed, but with the best products having an accuracy of ±5 ppb/K, this is insufficient. Currently, development is being conducted with a target of ±1 ppb/K, but an improvement beyond this level cannot be expected. In addition, the fact that this method requires specimens of a special shape (e.g. 100 mm (L)×6 mm ϕ), and the fact that, for the purpose of the measurements, destruction is entailed and surface distribution measurements with respect to actual specimens are impossible, etc., are problems from the point of view of materials evaluation methods and quality control.

Moreover, there are evaluation methods taking advantage of the fact that there are linear relationships between the coefficient of thermal expansion of an ultra-low-expansion glass and its other physical and chemical properties, ultrasonic velocity (Non-Patent Reference 3), chemical composition ratio and refractive index (Non-Patent Reference 1). For the evaluation of the coefficient of thermal expansion based on longitudinal-wave velocity measurements using the ultrasonic pulse echo method, chemical composition ratio measurements using the X-ray fluorescence method, the electron probe microanalysis method, the radio-frequency inductively-coupled plasma (ICP) emission analysis method or the like, and refractive index measurements etc. using an interferometer, respective accuracies of ±0.4 ppb/K, ±2 ppb/K, and ±0.023 ppb/K are obtained (Non-Patent Reference 1). However, as for the method based on measurements of the longitudinal wave velocity or the refractive index, this accuracy can not be obtained unless big specimens having a thickness of 100 mm are used, and also, only an average value can be obtained in the thickness direction. In this case, for the evaluation of specimens in which there exist periodic striae, which have developed into a problem in $TiO_2$—$SiO_2$ glass, it is impossible to obtain the distribution of thermal expansion coefficients corresponding to the periodicity of the striae. Also, in order to measure longitudinal-wave velocity, a measurement of the thickness of the specimen must also be performed, something which takes an unusual effort. Further, the dimensions of photomask substrates for EUVL use being 152 mm×152 mm×6.35 mm', a direct application to these dimensions causes the accuracy to decline markedly (approximately 18 times), due to the thickness.

Regarding technologies of evaluation of ultra-low-expansion glasses for EUVL use, it is required that it be possible to nondestructively evaluate a specimen with shapes actually used in EUVL systems and also, since optical systems are of a reflective type, that it be possible to make evaluations in the proximity of the surface of the specimen, and to evaluate the distribution of its characteristics, as well as to mention the requirements of a high measurement accuracy with respect to coefficients of thermal expansion and a high spatial resolution.

As a new technology for analyzing and evaluating substances and materials, an ultrasonic material characterization system was developed (Non-Patent Reference 4), and there is the possibility that this evaluation technology can overcome the aforementioned problems. In particular, a quantitative measurement method (the V(z) curve analysis method) using focused ultrasonic waves is valid. This is a method which performs a materials evaluation by measuring the propagation characteristics (phase velocity $V_{LSAW}$ and propagation attenuation $α_{LSAW}$) of leaky surface acoustic waves (LSAW) excited on a specimen surface loaded with water, or the propagation characteristics (phase velocity $V_{LSSCW}$ and propagation attenuation $α_{LSSCW}$) of leaky surface-skimming compressional waves (LSSCW). According to the present technique, a highly accurate measurement of the distribution of the characteristics of the whole glass substrate surface in a non-destructive and contactless manner is possible. For the measurements, an ultrasonic point-focus beam (PFB) and an ultrasonic line-focus beam (LFB) can be used, but here we will proceed with the explanation by considering an LFB ultrasonic material characterization system (refer to Non-Patent Reference 4 and Non-Patent Reference 5).

The LFB ultrasonic material characterization system can obtain the propagation characteristics of leaky acoustic waves propagating on the boundary between the water and the specimen by analyzing the V(z) curve obtained when the relative distance z between the LFB ultrasonic device and the specimen is changed. FIG. 1 is a cross-sectional view, showing the principle of measurement, of a system including an ultrasonic device, consisting of an ultrasonic transducer 1, an LFB acoustic lens 2, and a glass specimen 3. The focal point, which would be situated in the water, is taken as the origin Oxy for the coordinate axes, as shown in the figure. The ultrasonic plane wave excited by ultrasonic transducer 1 is focused into a wedge shape by LFB acoustic lens 2 and irradiated onto the surface of glass specimen 3 through a water coupler 4. In case the specimen is closer to the ultrasonic device side than a focal plane 5 is, the components predominantly contributed to the output of ultrasonic transducer 1 among the reflected waves from glass substrate 3 will, by the effect of the opening surface of acoustic lens 2, only be the components taking paths P0, P1, P2 approximately shown in FIG. 1. The P0 component is the component directly reflected from the specimen, the P1 component is the component incident on glass specimen 3 at a critical LSAW excitation angle $\theta_{LSAW}$ propagated as a leaky surface acoustic wave (LSAW) along the surface of glass specimen 3. The P2 component is the component incident on glass specimen 3 at a critical LSSCW excitation angle $\theta_{LSSCW}$ propagated as a leaky surface-skimming compressional wave (LSSCW) along the surface of glass specimen 3. The transducer output V(z) is obtained as the interference waveform of these three components. In the V(z) curve analysis model (Non-Patent Reference 5), it is approximately expressed by the following equation:

$$V(z)=V_I(z)(LSAW)+V_I(z)(LSSCW)+V_L(z) \quad (1)$$

where $$V_L(z)=V_L'(z)+\Delta V_L(z) \quad (2)$$

and $V_I(z)(LSAW)$ and $V_I(z)(LSSCW)$ are the respective LSAW and LSSCW interference components, and $V_L(Z)$ is the component reflecting the characteristics of the ultrasonic device. Also, $\Delta V_L(Z)$ is the difference of $V_L(z)$ with respect to $V_L'(z)$ of a specimen with no excitation of leaky acoustic waves (e.g. Teflon®). $V_I(z)(LSAW)$ and $V_I(z)(LSSCW)$ are extracted on the basis of the V(z) curve analysis method (Non-Patent Reference 5), and their interference intervals $\Delta z_{LSAW}$ and $\Delta z_{LSSCW}$ are obtained and substituted for $\Delta z$ in Eq. (3), which follows, to obtain the LSAW velocity $V_{LSAW}$ and the LSSCW velocity $V_{LSSCW}$.

$$V = \frac{V_W}{\sqrt{1-\left(1-\frac{V_W}{2f\Delta z}\right)^2}} \quad (3)$$

where f is the ultrasonic frequency and $V_W$ is the longitudinal velocity in water. $V_W$ can be obtained, according to Non-Patent Reference 6, from the water coupler temperature measured by means of a thermocouple at the time of the V(z) curve measurement.

Next, the procedure of extracting the LSAW velocity $V_{LSAW}$ and the LSSCW velocity $V_{LSSCW}$ by the V(z) curve analysis method will be explained using the flowchart shown in FIG. 2. It will be explained by considering the V(z) curve measured at f=225 MHz for ultra-low-expansion glass #1 (made by Company A).

Step S1: Normally, the V(z) curve measured on a decibel scale (FIG. 3A) is converted into a digital waveform, loaded to a computer, and converted to a linear scale (FIG. 3B).

Step S2: $V_W$ is obtained with Non-Patent Reference 6 from the water coupler temperature $T_W$ measured at the same time as the V(z) curve.

Step S3: The $V_L'(z)$ curve (e.g. V(z) curve measured for Teflon® (FIG. 3C)), which is a curve approximating the $V_L(Z)$ curve reflecting the characteristics of the ultrasonic device, is obtained, and by subtracting from the V(z) curve of Step S1, the $V_I'(z)$ curve is obtained (FIG. 4A). Consequently, the result from Eqs. (1) and (2) is that $$V_I'(z) = V(z) - V_L'(z) \quad (3a)$$
$$= V_I(z)(LSAW) + V_I(z)(LSSCW) + \Delta V_L(z)$$

is obtained.

Step S4: For the $V_I'(z)$ curve of Step S3, the interference component due to LSAW (the interference interval $\Delta z_{LSAW}$) is removed by using a digital filter, and the $V_I''(z)$ curve expressing the low-frequency component including the direct current component is extracted (FIG. 5A). Consequently, from Eq. (3a) above, the result is that $$V_I''(z)=V_I'(z)-V_I(z)(LSAW)=V_I(z)(LSSCW)+\Delta V_L(Z) \quad (3b)$$

is obtained.

Step S5: By subtracting the $V_I''(z)$ curve obtained in Step S4 from the $V_I'(z)$ curve obtained in Step S3, the interference output curve $V_I(z)(LSAW)$ needed for the LSAW analysis is obtained (FIG. 4B). Specifically, $$V_I(z)(LSAW)=V_I'(z)-V_I''(z). \quad (3c)$$

Step S6: By performing an FFT (Fast Fourier Transform) analysis of the $V_I(z)(LSAW)$ curve obtained in Step S5, in the FFT analysis range shown in FIG. 4B, a wavenumber spectrum distribution is obtained (FIG. 4C), and from its peak value, the interference interval $\Delta z_{LSAW}$ is determined.

Step S7: From $\Delta z_{LSAW}$ obtained in Step S6 and $V_W$ obtained in Step S2, $V_{LSAW}$ is determined from Eq. (3).

Step S8: From $V_I''(z)$ obtained in Step S4, the interference component due to LSSCW (the interference interval $\Delta z_{LSSCW}$) is removed by using a digital filter, and the $\Delta V_L(z)$ curve including the direct current component is extracted (FIG. 5B).

Step S9: By subtracting $\Delta V_L(Z)$ obtained in Step S8 from $V_I''(z)$ obtained in Step S4, the interference output curve $V_I(z)(LSSCW)$ required for the LSSCW analysis is obtained (FIG. 5C).

Step S10: By performing an FFT analysis in the FFT analysis range shown in FIG. 5C of the $V_I(z)(LSSCW)$ curve obtained in Step S9, the wavenumber spectrum distribution (FIG. 5D) is obtained, and the interference interval $\Delta z_{LSSCW}$ is determined from its peak value.

Step S11: From $\Delta z_{LSSCW}$ obtained in Step S10 and $V_W$ obtained in Step S2, $V_{LSSCW}$ is determined from Eq. (3).

Since, so far, in the materials evaluation using $V_{LSAW}$, materials having small acoustic losses and exhibiting no velocity dispersion (e.g. single crystal materials) were mainly targeted, an analytical method with respect to ultra-low-expansion glasses, which have the possibility of having large such losses and exhibiting velocity dispersion, was not developed. Since the leaky acoustic wave velocities ($V_{LSAW}$ and $V_{LSSCW}$) obtained by the V(z) curve analysis method depend on the system and the ultrasonic device and are shifted from the true value, it is necessary to perform an absolute calibration using a standard specimen, as shown in Non-Patent Reference 7. In that calibration method, a numerical calculation of the propagation characteristics of the leaky acoustic waves is necessary, but the calculation was performed, based on Non-Patent Reference 8 or Non-Patent Reference 9, by assuming the specimen and the water to be lossless and by disregarding velocity dispersion and the attenuation coefficients. That is to say that a preparation method for an appropriate standard specimen with respect to materials with the possibility of having large acoustic losses and presenting velocity dispersion has not been investigated.

Evaluation methods of the coefficient of thermal expansion based on conventional methods had the problems of having a low measurement accuracy, not being able to non-destructively evaluate specimen with shapes actually utilized, and not being able to measure distribution characteristics. Moreover, as to materials evaluation based on an LFB ultrasonic material characterization system, for which there can be expected a higher measurement accuracy than for conventional methods and the implementation, non-destructively and without contact, of measurements of the distribution characteristics in the surface of material substrates, an analytical method with respect to ultra-low-expansion glass materials having the possibility of exhibiting velocity dispersion characteristics has not been developed.

Patent Reference 1: Japanese Patent Application Laid Open No. 2002-257502.

Non-Patent Reference 1: K. E. Hrdina, B. G. Ackerman, A. W. Fanning, C. E. Heckle, D. C. Jenne, and W. D. Navan, "Measuring and tailoring CTE within ULE Glass," Proc. SPIE, Emerging Lithographic Technologies VII, Vol. 5037, pp. 227–235 (2003).

Non-Patent Reference 2: I. Mitra, M. J. Davis, J. Alkemper, R. Muller, H. Kohlmann, L. Aschke, E. Morsen, S. Ritter, H. Hack, and W. Pannhorst, "Thermal expansion behavior of proposed EUVL substrate materials," Proc. SPIE, Vol. 4688, pp. 462–468 (2002).

Non-Patent Reference 3: H. E. Hagy and W. D. Shirkey, "Determining absolute thermal expansion of titania-silica glasses: a refined ultrasonic method," Appl. Opt., Vol. 14, pp. 2099–2103 (1975).

Non-Patent Reference 4: J. Kushibiki, Y. Ono, Y. Ohashi, and M. Arakawa, "Development of the line-focus-beam ultrasonic material characterization system," IEEE Trans. Ultrason., Ferroelect., Freq. Contr., Vol. 49, pp. 99–113 (2002).

Non-Patent Reference 5: J. Kushibiki and N. Chubachi, "Material characterization by line-focus-beam acoustic microscope," IEEE Trans. Sonics and Ultrason., Vol. SU-32, pp. 189–212 (1985).

Non-Patent Reference 6: W. Kroebel and K.-H. Mahrt, "Recent results of absolute sound velocity measurements in pure water and sea water at atmospheric pressure," Acustica, Vol. 35, pp. 154–164 (1976).

Non-Patent Reference 7: J. Kushibiki and M. Arakawa, "A method for calibrating the line-focus-beam acoustic microscopy system," IEEE Trans. Ultrason., Ferroelect., Freq. Contr., Vol. 45, pp. 421–430 (1998).

Non-Patent Reference 8: J. J. Campbell and W. R. Jones, "Propagation of surface waves at the boundary between a piezoelectric crystal and a fluid medium," IEEE Trans. Sonics Ultrason., Vol. SU-17, pp. 71–76 (1970).

Non-Patent Reference 9: I. A. Viktrov, "Rayleigh and Lamb Waves: Physical Theory and Applications", (Plenum, New York, 1967), Chap. I, pp. 46–57.

Non-Patent Reference 10: A. O. Williams, Jr., "The piston source at high frequencies," J. Acoust. Soc. Am., Vol. 23, pp. 1–6 (1951).

Non-Patent Reference 11: J. Kushibiki, R. Okabe, and M. Arakawa, "Precise measurements of bulk-wave ultrasonic velocity dispersion and attenuation in solid materials in the VHF range," J. Acoust. Soc. Am., Vol. 113, pp. 3171–3178 (2003).

Non-Patent Reference 12: M. Arakawa, J. Kushibiki, and N. Aoki, "An evaluation of effective radiuses of bulk-wave ultrasonic transducers as circular piston sources for accurate velocity measurements," IEEE Trans. Ultrason., Ferroelect., Freq. Contr., Vol. 51, pp. 496–501 (2004).

Non-Patent Reference 13: J. M. M. Pinkerton, "The absorption of ultrasonic waves in liquids and its relation to molecular constitution," Proc. Phys. Soc., Vol. B62, pp. 129–141 (1949).

Non-Patent Reference 14: Y. Hashimoto, N. Akashi, J. Kushibiki, "Measurements of ultrasonic attenuation coefficients of water in VHF/UHF range," Tech. Rep. IEICE, Vol. US97-50, pp. 37–42 (1997).

Non-Patent Reference 15: J. Kushibiki, M. Arakawa, and R. Okabe "High-accuracy standard specimens for the line-focus-beam ultrasonic material characterization system," IEEE Trans. Ultrason., Ferroelect., Freq. Contr., Vol. 49, pp. 827–835 (2002).

Non-Patent Reference 16: D. Gerlich and M. Wolf, "Thermoelastic properties of Zerodur glass-ceramic," J. Non-Cryst. Solids, Vol. 27, pp. 209–214 (1978).

SUMMARY OF THE INVENTION

Accordingly, there is provided, in the present invention, a method of preparing general standard specimens (enabling the calculation of theoretical values of the leaky acoustic wave velocities for a selected specimen substrate by measuring the acoustic velocities, the attenuation coefficients and the density for the specimen substrate) and calibrating measurement systems, in order to make it possible to perform an analytical evaluation of the coefficient of thermal expansion of materials capable of exhibiting a velocity dispersion characteristic, like ultra-low-expansion glasses, using leaky acoustic wave velocities measured by means of an ultrasonic material characterization system, and there is provided an evaluation method for coefficients of thermal expansion based on the obtained elastic property results.

The evaluation method according to this invention for a coefficient of thermal expansion of an ultra-low-expansion glass material includes:

(a) a step of measuring, in the used ultrasonic frequency range, the longitudinal velocity and attenuation coefficient, the shear velocity and attenuation coefficient, and the density, of a standard specimen of an ultra-low-expansion glass material;

(b) a step of calculating a first leaky acoustic wave characteristic with respect to the aforementioned standard specimen, from the aforementioned acoustic velocities, attenuation coefficients, and density;

(c) a step of obtaining, by measuring the leaky acoustic wave interference signal curve V(z) with respect to the aforementioned standard specimen, a second leaky acoustic wave characteristic from that V(z) curve;

(d) a step of obtaining, as a calibration coefficient, the ratio of the aforementioned first leaky acoustic wave characteristic calculated in the aforementioned step (b) and the aforementioned second leaky acoustic wave characteristic obtained from the aforementioned V(z) curve in step (c);

(e) a step of measuring a V(z) curve with respect to the measured specimen of the ultra-low-expansion glass material and obtaining from that V(z) curve a third leaky acoustic wave characteristic;

(f) a step of calibrating, with the aforementioned calibration coefficient, the aforementioned third leaky acoustic wave characteristic obtained for the aforementioned measured specimen;

(g) a step of obtaining the relationship between the coefficient of thermal expansion of the aforementioned ultra-low-expansion glass material and the absolutely calibrated aforementioned third leaky acoustic wave characteristic; and (h) a step of measuring a fourth leaky acoustic wave characteristic with respect to the ultra-low-expansion glass specimen under evaluation, and, based on the aforementioned relationship, evaluating the coefficient of thermal expansion.

BRIEF DESCRIPTION OF THE DRAWINGS

FIG. 10A is a diagram showing the results of measuring the bulk wave acoustic velocities with respect to ultra-low-expansion glass #1-1;

FIG. 10B is a diagram showing the results of measuring the bulk wave acoustic velocities with respect to ultra-low-expansion glass #2-1;

FIG. 10C is a diagram showing the results of measuring the bulk wave acoustic velocities with respect to synthetic silica glass #3-1;

FIG. 10D is a diagram showing the result of measuring the attenuation coefficients with respect to ultra-low-expansion glass #1-1;

FIG. 10E is a diagram showing the result of measuring the attenuation coefficients with respect to ultra-low-expansion glass #2-1;

FIG. 10F is a diagram showing the result of measuring the attenuation coefficients with respect to synthetic silica glass #3-1;

FIG. 14 is a diagram showing the chemical composition ratios for ultra-low-expansion glasses #1-1 and #2-1, and synthetic silica glass #3-1;

FIG. 15 is a diagram showing the bulk-wave acoustic properties at 225 MHz of ultra-low-expansion glass #1-1 and synthetic silica glass #3-1;

FIG. 16 is a diagram showing the LSAW velocity sensitivities and resolutions for physical/chemical properties of ultra-low-expansion glass #1;

FIG. 17 is a diagram showing the LSSCW velocity sensitivities and resolutions for physical/chemical properties of ultra-low-expansion glass #1;

FIG. 18A is a diagram showing a glass ingot including periodic striae;

FIG. 18B is a diagram showing specimen #1-2 for which the striae are parallel to the glass substrate surface;

FIG. 18C is a diagram showing specimen #1-3 for which the striae are perpendicular to the glass substrate surface;

FIG. 25 is a diagram showing the chemical composition ratios for ultra-low-expansion glasses #2;

FIG. 26 is a diagram showing the densities for ultra-low-expansion glasses #2;

FIG. 30 is a diagram showing the longitudinal velocity sensitivities and resolutions for physical/chemical properties of ultra-low-expansion glass #1;

FIG. 31 is a diagram showing the measurement accuracies of the LSAW velocities, the LSSCW velocities, and the longitudinal velocities, as well as the resolutions, based on the velocity measurements, for the coefficient of thermal expansion, the $TiO_2$ concentration, and the density.

DETAILED DESCRIPTION OF THE PREFERRED EMBODIMENT

First, an explanation will be given of a method of preparing a standard specimen for absolute calibration of an LFB ultrasonic material characterization system for the case of performing a normal evaluation with respect to an isotropic material exhibiting a velocity dispersion characteristic (normal glass material with no striae). For a substrate used as a standard specimen, the frequency dependency of the acoustic velocities and the attenuation coefficients, of the bulk waves (longitudinal wave and shear wave), as well as the density, are measured by the method mentioned hereinafter.

Figure 6:
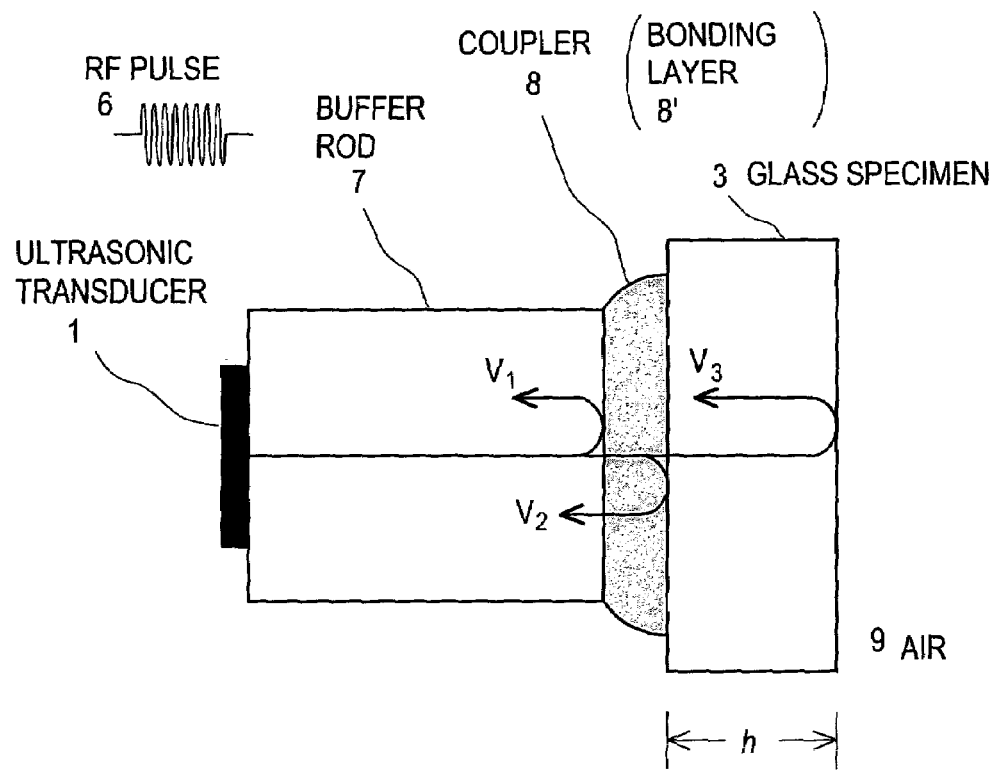
FIG. 6 is a diagram showing an experimental configuration for measurement of bulk-wave acoustic properties.
Figure 7:
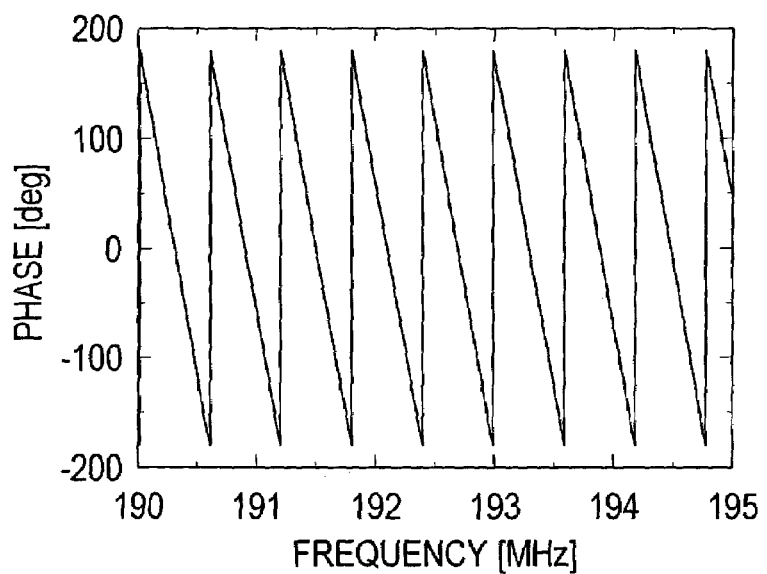
FIG. 7 is a diagram showing the phase φ of the ratio $V_3/V_2$ measured by a complex-mode measurement method.

As a measurement method for the bulk-wave acoustic properties (acoustic velocity and attenuation coefficient), a complex-mode measurement method using a radio-frequency (RF) tone burst pulse 6 will be taken as an example and explained. The experimental configuration for the measurement of the bulk-wave acoustic velocities is shown in FIG. 6. An ultrasonic device with a buffer rod 7 (e.g. of synthetic silica glass), equipped on one end face with an ultrasonic transducer 1, is used. In the case of longitudinal velocity measurements, by using pure water as a coupler 8, adjusting the propagation length of the coupler so that a reflected signal $V_2$ from the front face of glass specimen 3 and a reflected signal $V_3$ from its back face do not overlap with a spurious signal in the time domain, and measuring the amplitude of $V_3/V_2$, $|V_3/V_2|$, and phase φ at each frequency (shown in FIG. 7), the specimen longitudinal velocity $V_1$ and the longitudinal attenuation coefficient $\alpha_1$ are respectively obtained from Eqs. (4) and (5).

$$V_{l_0} = -\frac{2\omega h}{\phi - \pi - \Delta\theta} \quad (4)$$

$$\alpha_{l_0} = \frac{1}{2h}\ln\left\{\left|\frac{V_2}{V_3}\right| \cdot \left|\frac{T_{23} \cdot T_{32}}{R_{23}}\right|\right\} - \frac{1}{2h}\ln\left|\frac{ATT_2}{ATT_3}\right| \quad (5)$$

where, ω is the angular frequency, h is the thickness of the specimen, π is the phase rotation in the case of reflection at the back face of the specimen, Δθ is the difference in phase advance due to diffraction of the signals $V_2$ and $V_3$, and $|ATT_3/ATT_2|$ is the diffraction loss ratio. $T_{23}$ and $T_{32}$ are the respective transmission coefficients from the coupler to the specimen and from the specimen to the coupler, and $R_{23}$ is the reflection coefficient of the specimen seen from the coupler. The influence of diffraction ($\Delta\theta$ and $ATT_3/ATT_2$) is corrected with a numerical calculation using the exact integral expression of Williams (Non-Patent Reference 10). Since silicate glass normally exhibits velocity dispersion in the VHF range, the influence of the velocity dispersion is taken into account in performing the diffraction correction (Non-Patent Reference 11). Moreover, in order to accurately obtain the frequency characteristics of the acoustic properties, the effective diameter of the ultrasonic transducer used in the measurement as a circular piston sound source is obtained, and the influence of the diffraction is corrected (Non-Patent Reference 12). The specimen thickness is measured e.g. by a contact-type digital length gauging system with an optical linear encoder built in (Patent Reference 1).

As shear waves cannot propagate in water, the measurements of the shear-wave acoustic properties are performed with the specimen bonded with salol (phenyl salicylate) to buffer rod 7. In FIG. 6, the bonding layer 8' replacing coupler 8 is indicated in parentheses. At this time, since the salol layer is prepared so as to be exceedingly thin, with a thickness of less than 1 µm, there only occurs a time difference between signal $V_1$ and signal $V_2$ which is much shorter than the width of RF pulse 6, so signal $V_1$ and signal $V_2$ can not be separated in the time domain. For this reason, if the multiple reflection components in the bonding layer overlap in the time domain and one considers this as one pulse, the result is that it is equivalent to there occurring an amplitude change $A_{BL}$ and a phase change $\theta_{BL}$ in case this pulse is transmitted or reflected by bonding layer 8'. By estimating the acoustic parameters (acoustic velocity, attenuation coefficient, density, and thickness) of bonding layer 8' from the reflection coefficient of glass specimen 3 seen from buffer rod 7, $A_{BL}$ and $\theta_{BL}$ are calculated. The shear velocity $V_s$ and the shear-wave attenuation coefficient $\alpha_s$ are respectively obtained by Eqs. (6) and (7), $$V_s = -\frac{2\omega h}{\phi - \pi - \Delta\theta - \theta_{BL}} \text{ and} \quad (6)$$

$$\alpha_s = \frac{1}{2h}\ln\left\{\left|\frac{V_2}{V_3}\right|\cdot A_{BL}\right\} - \frac{1}{2h}\ln\left|\frac{ATT_2}{ATT_3}\right|. \quad (7)$$

The density $\rho$ is measured based on the Archimedes principle.

Since silicate glass, whose main component is $SiO_2$, has large acoustic losses in the VHF and UHF ranges and may exhibit velocity dispersion, it is necessary to take into account the influence of this in the calculation of the propagation characteristics of leaky acoustic waves. Consequently, in order to rigorously obtain the leaky acoustic wave velocity, the velocity dispersion and the attenuation coefficient need to be taken into account when performing the numerical calculation. In the case of isotropic solids, the numerical calculation of the leaky acoustic wave velocity $V_{LSAW}$ (or $V_{LSSCW}$) is carried out using Eqs. (8) to (15) mentioned hereinafter.

$$4\beta_1\beta_2 - (1+\beta_2^2)^2 = -\frac{\rho_w}{\rho}\frac{\beta_1}{\beta_3}(1-\beta_2^2)^2, \quad (8)$$

where $\rho$ and $\rho_w$ are respectively the densities of the specimen and water, and $\beta_1$, $\beta_2$, and $\beta_3$ are expressed as mentioned hereinafter.

$$\beta_1 = \sqrt{1-\left(\frac{k_l}{k}\right)^2} \quad (9)$$

$$\beta_2 = \sqrt{1-\left(\frac{k_s}{k}\right)^2} \quad (10)$$

$$\beta_3 = \sqrt{1-\left(\frac{k_W}{k}\right)^2} \quad (11)$$

Here, $k$, $k_1$, $k_s$, and $k_W$ are respectively the complex wavenumbers of LSAW (or LSSCW), the longitudinal wave, the shear wave, and the longitudinal wave in water, and are expressed as mentioned hereinafter.

$$k = \frac{\omega}{V_{LSAW}}(1+j\alpha_{LSAW}) \quad (12)$$

$$k_l = \frac{\omega}{V_l} + j\alpha_l \quad (13)$$

$$k_s = \frac{\omega}{V_s} + j\alpha_s \quad (14)$$

$$k_W = \frac{\omega}{V_W} + j\alpha_W \quad (15)$$

By substituting Eqs. (12) to (15) in Eqs. (9) to (11) and by substituting $\beta_1$, $\beta_2$, and $\beta_3$ in Eq. (8), one obtains an equation related to $V_{LSAW}$ (or $V_{LSSCW}$), which can be found by a numerical analysis method (e.g. by Newton's method).

Here, $\alpha_{LSAW}$ (or $\alpha_{LSSCW}$) and $\alpha_W$ are, respectively, the normalized LSAW (or LSSCW) propagation attenuation factor and the attenuation coefficient in water. As for the acoustic parameters of water in the numerical calculation, the acoustic velocity of water is obtained from the temperature of the water coupler, $T_W$, during the measurement of the V(z) curve for the standard specimen and from Non-Patent Reference 6, and the attenuation coefficient of water is obtained from $T_W$ and Non-Patent Reference 13. Regarding the velocity dispersion of water, it can be disregarded up to 1 GHz, and the attenuation coefficient is proportional to the square of the frequency up to 1 GHz (Non-Patent Reference 14).

Next, in order to obtain the absolute value of the leaky acoustic wave velocity measured by the LFB ultrasonic material characterization system, the calibration procedure using the standard specimen will be explained using the flowchart shown in FIG. 8.

Step S1: In the desired ultrasonic frequency range and temperature range used for the V(z) curve measurements, the longitudinal velocity $V_l(f)$ and the attenuation coefficient $\alpha_l(f)$, the shear velocity $V_s(f)$ and the attenuation coefficient $\alpha_s(f)$, as well as the density $\rho$, are measured for the standard specimen, with high accuracy.

Figure 2:
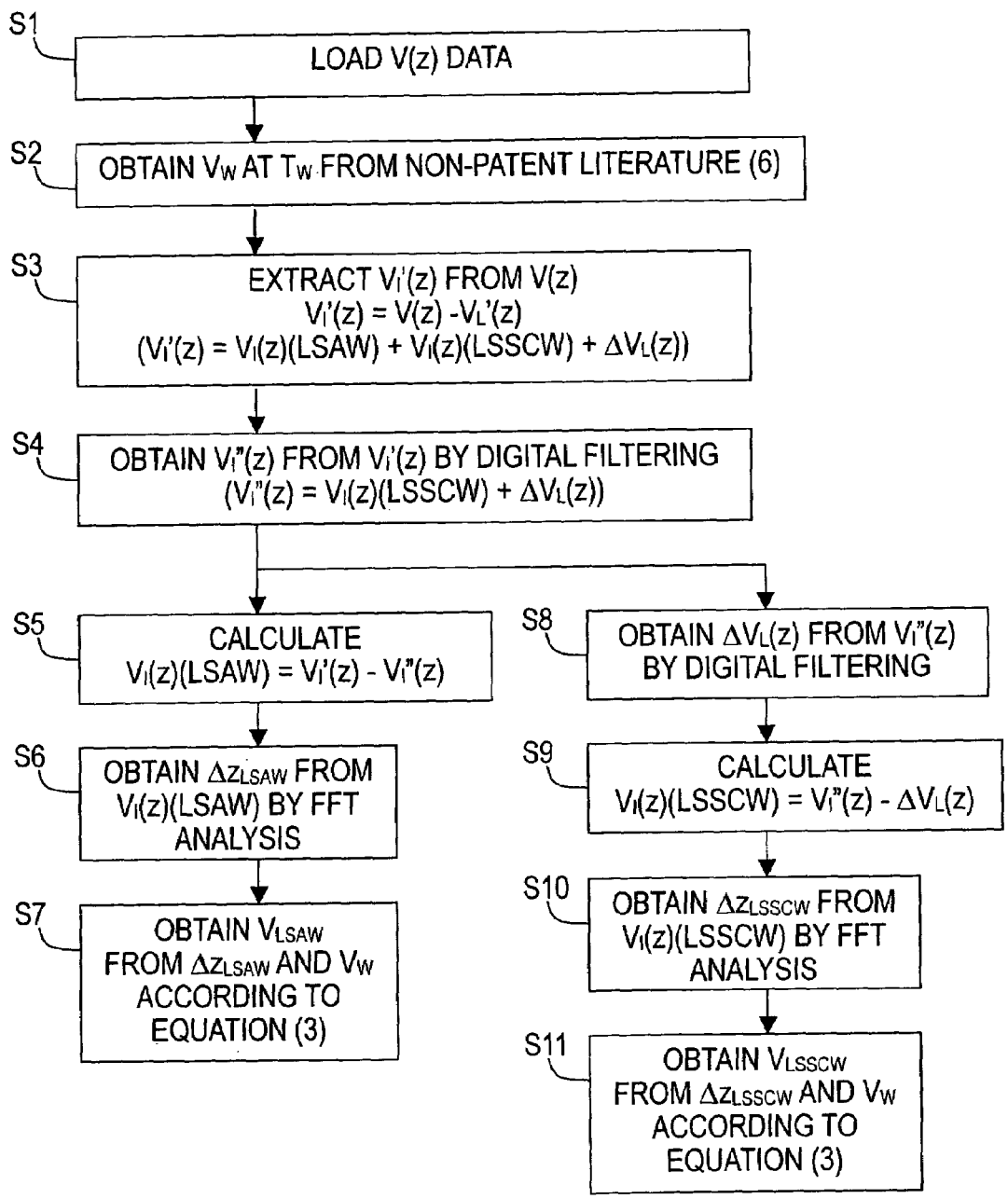
FIG. 2 is a flowchart for the V(z) curve analysis method.
Figure 3A:
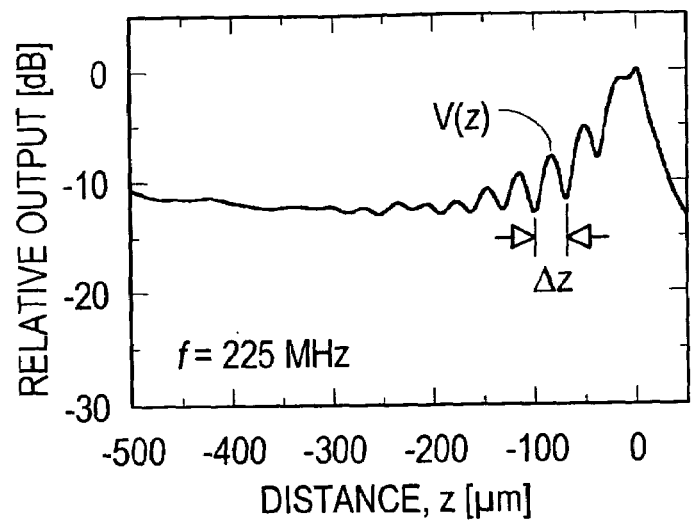
FIG. 3A is a diagram showing an example of a V(z) curve.
Figure 3B:
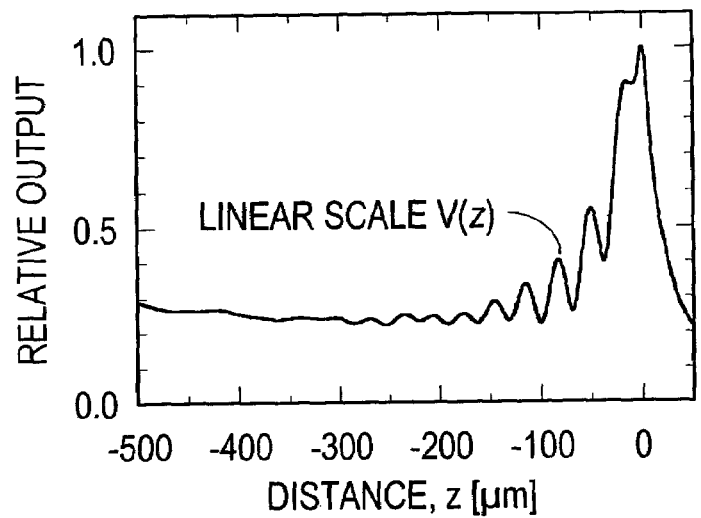
FIG. 3B is a diagram in which the V(z) curve of FIG. 3A has been converted to a linear scale.
Figure 3C:
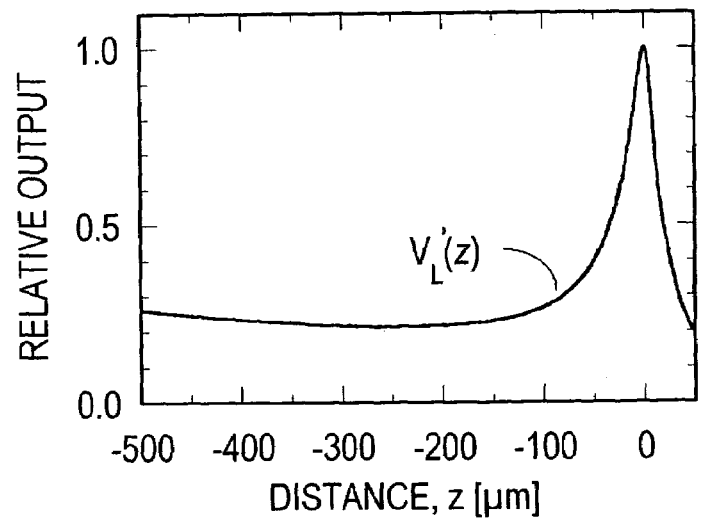
FIG. 3C is a diagram showing the $V_L'(z)$ curve measured with respect to Teflon®, which is a curve approximating the $V_L(z)$ curve.

Step S2: The V(z) curve is measured for the measured specimen, and $\Delta z_{LSAW}$(measured) and $\Delta z_{LSSCW}$(measured) are obtained with the V(z) curve analysis method of FIG. 2. From the temperature $T_W$(measured) during the V(z) curve measurement at this time, the value, $V_W$ obtained according to Non-Patent Reference 6 is taken as $V_W$(measured).

Step S3: At the same frequency as that used during the measurement of the measured specimen, the V(z) curve is measured for the standard specimen, and $\Delta z_{LSAW}$(std.meas.) and $\Delta z_{LSSCW}$(std.meas.) are obtained by the V(z) curve analysis method. From the temperature $T_W$(std.meas.) during the V(z) curve measurement at this time, the value for $V_W$ obtained with Non-Patent Reference 6 is taken to be $V_W$(std.meas.), and the value for $\alpha_W$ obtained with Non-Patent Reference 13 is taken to be $\alpha_W$(std.meas.).

Step S4: Using the acoustic velocities, the attenuation coefficients, and the density of the standard specimen obtained in Step S1, the LSAW velocity $V_{LSAW}$(std.calc.) at the temperature and frequency at which the V(z) curve was measured is calculated from Eqs. (8) to (15).

Step S5: From $V_{LSAW}$(std.calc.) obtained in Step S4 and $V_W$(std.meas.) obtained in Step S3, $\Delta z_{LSAW}$(std.calc.) is calculated using Eq. (3).

Step S6: From $\Delta z_{LSAW}$(std.meas.) obtained in Step S3 and $\Delta z_{LSAW}$(std.calc.) obtained in Step S5, the calibration coefficient $K_z$(LSAW) is obtained as a result of Eq. (16), which follows.

$$K_Z(LSAW) = \frac{\Delta z_{LSAW}(std.calc.)}{\Delta z_{LSAW}(std.meas.)} \quad (16)$$

Step S7: As a result of Eq. (17), which follows, $\Delta z_{LSAW}$(measured) obtained in Step S2 for the measured specimen is calibrated to obtain $\Delta z_{LSAW}$(calibrated).

$$\Delta z_{LSAW}(\text{calibrated}) \square K_Z(LSAW) \times \Delta z_{LSAW}(\text{measured}) \quad (17)$$

Step S8: By substituting in Eq. (3) the values for $\Delta z_{LSAW}$(calibrated) obtained in Step S7 and $V_W$(measured) obtained in Step S2, the calibrated $V_{LSAW}$(calibrated) is obtained.

Step S9: By using the acoustic velocities, the attenuation coefficients, and the density of the standard specimen, the LSSCW velocity $V_{LSSCW}$(std.calc.) at the temperature and frequency at which the V(z) curve was measured is calculated from Eqs. (8) to (15).

Step S10: From $V_{LSSCW}$(std.calc.) obtained in Step S9 and $V_W$(std.meas.) obtained in Step S3, $\Delta z_{LSSCW}$(std.calc.) is calculated using Eq. (3).

Step S11: The calibration coefficient $K_z$(LSSCW) is obtained as a result of Eq. (18), which follows.

$$K_Z(LSSCW) = \frac{\Delta z_{LSSCW}(std.calc.)}{\Delta z_{LSSCW}(std.meas.)} \quad (18)$$

Step S12: By Eq. 19, which follows, $\Delta z_{LSSCW}$(measured), obtained in Step S2 for the measured specimen is calibrated to obtain $\Delta z_{LSSCW}$(calibrated).

$$\Delta z_{LSSCW}(\text{calibrated}) \square K_Z(LSSCW) \times \Delta z_{LSSCW}(\text{measured}) \quad (19)$$

Step S13: By substituting in Eq. (3) the values for $\Delta z_{LSSCW}$(calibrated) obtained in Step S12 and $V_W$(measured) obtained in Step S2, the calibrated $V_{LSSCW}$(calibrated) is obtained.

Figure 9:
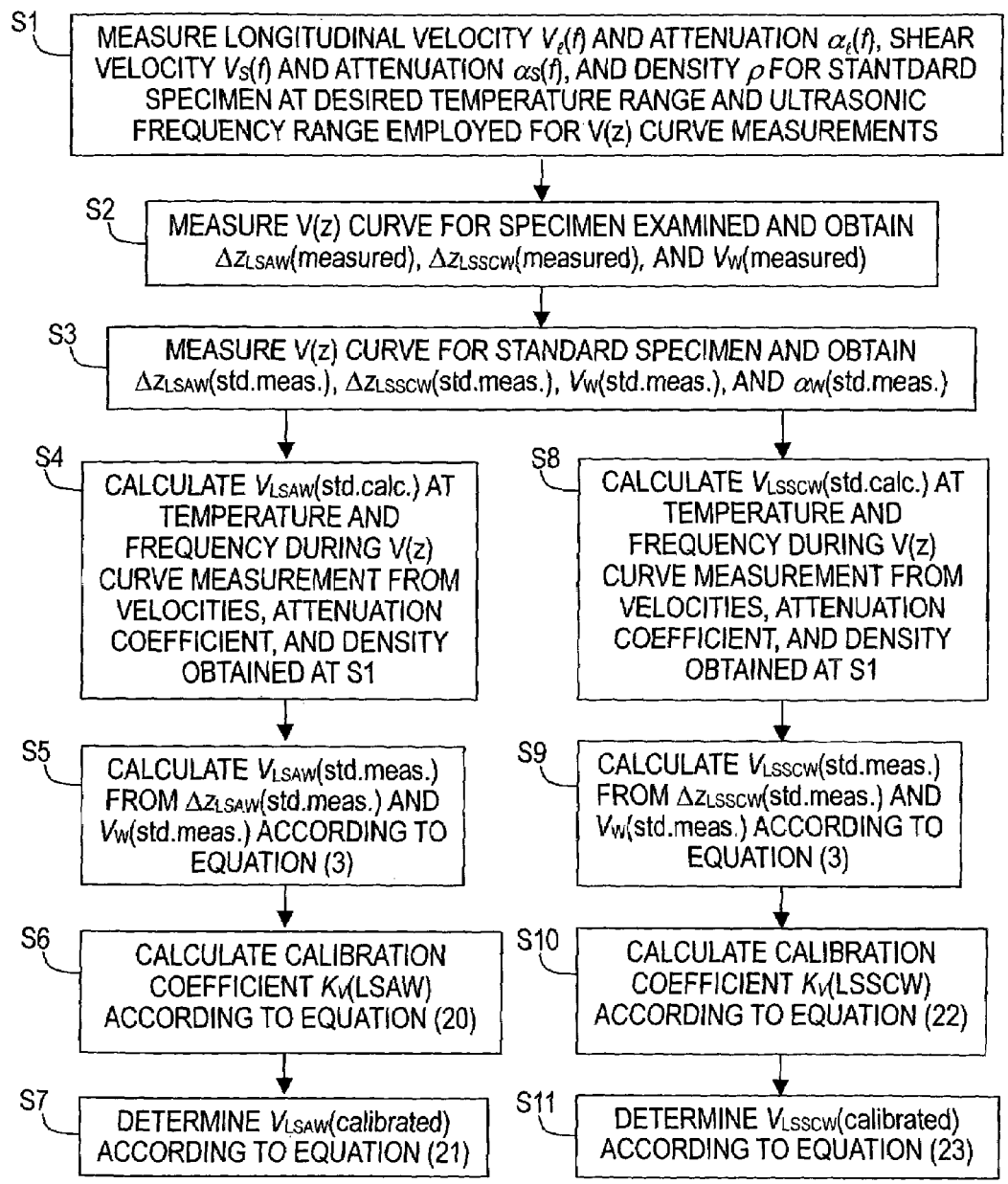
FIG. 9 is another flowchart for the calibration of an LFB ultrasonic material characterization system.

In the foregoing, a case was shown in which the calibration coefficient is determined by using $\Delta z_{LSAW}$ and $\Delta z_{LSSCW}$ of the standard specimen, but the calibration coefficient may also be determined by using $V_{LSAW}$ and $V_{LSSCW}$ of the standard specimen. That example will now be explained with reference to FIG. 9.

Figure 8:
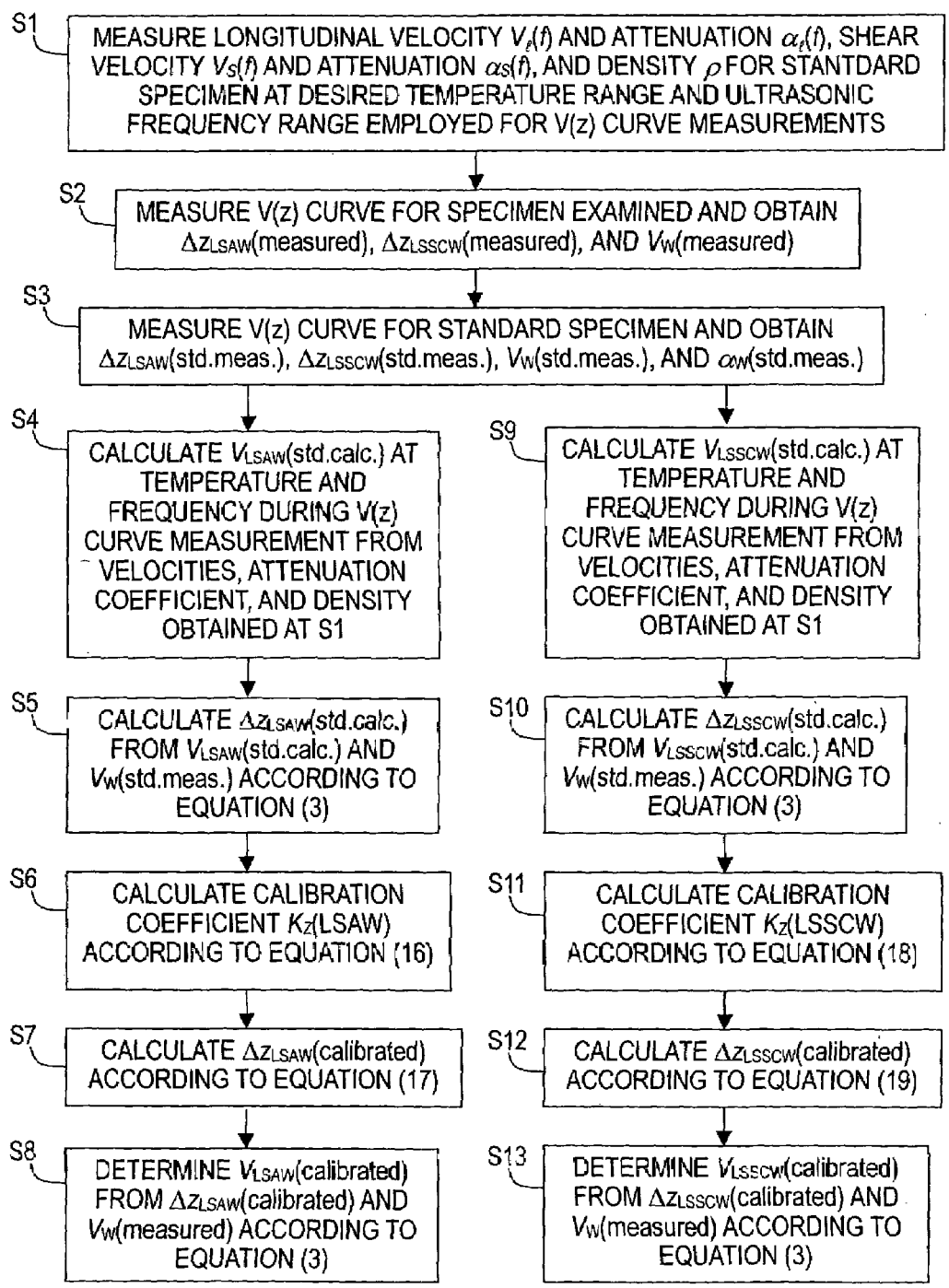
FIG. 8 is a flowchart for the calibration of an LFB ultrasonic material characterization system.

Since Steps S1, S2, and S3 are the same as the case in FIG. 8, their explanation will be omitted.

Step S4: Using the acoustic velocities, the attenuation coefficient, and the density of the standard specimen, the LSAW velocity $V_{LSAW}$(std.calc.) at the temperature and frequency at which the V(z) curve was measured is calculated from Eqs. (8) to (15).

Step S5: From $\Delta z_{LSAW}$(std.meas.) and $V_W$(std.meas.) obtained in Step S3, $V_{LSAW}$(std.meas.) is calculated using Eq. (3).

Step S6: From $V_{LSAW}$(std.calc.) obtained in Step S4 and $V_{LSAW}$(std.meas.) obtained in Step S5, the calibration coefficient $K_V$(LSAW) is obtained with Eq. (20), which follows.

$$K_V(LSAW) = \frac{V_{LSAW}(std.calc.)}{V_{LSAW}(std.meas.)} \quad (20)$$

Step S7: By Eq. (21), which follows, $V_{LSAW}$(measured) is calibrated to obtain $V_{LSAW}$(calibrated).

$$V_{LSAW}(\text{calibrated}) \square K_V(LSAW) \times V_{LSAW}(\text{measured}) \quad (21)$$

Step S8: Using the acoustic velocities, the attenuation coefficients, and the density of the standard specimen, the LSSCW velocity $V_{LSSCW}$(std.calc.) at the temperature and frequency at which the V(z) curve was measured is calculated from Eqs. (8) to (15).

Step S9: From $\Delta z_{LSSCW}$(std.meas.) and $V_W$(std.meas.) obtained in Step S3, $V_{LSSCW}$(std.meas.) is calculated using Eq. (3).

Step S10: The calibration coefficient $K_V$(LSSCW) is obtained by Eq. (22), which follows.

$$K_V(LSSCW) = \frac{V_{LSSCW}(std.calc.)}{V_{LSSCW}(std.meas.)} \quad (22)$$

Step S11: From Eq. (23), which follows, $V_{LSSCW}$(measured) is calibrated to obtain $V_{LSSCW}$(calibrated).

$$V_{LSSCW}(\text{calibrated}) \square K_V(LSSCW) \times V_{LSSCW}(\text{measured}) \quad (23)$$

Finally, an explanation will be given of the evaluation method for ultra-low-expansion glass materials using the dispersion characteristics of the absolutely calibrated LSAW velocity and LSSCW velocity, obtained as mentioned above.

As a first evaluation method, in FIG. 8, the ratio $V_s(f)/V_{LSAW}$(std.calc.) of the shear velocity, obtained in Step S1, to $V_{LSAW}$(std.calc.) for the standard specimen, obtained in Step S4, and the ratio $V_l(f)/V_{LSSCW}$(std.calc.) of the longitudinal velocity, obtained in Step S1, to $V_{LSSCW}$(std.calc.) for the standard specimen, obtained in Step S9, are obtained. Similarly, the ratios $\rho/V_{LSAW}$(std.calc.), $\rho/V_{LSSCW}$(std.calc.) of the density, obtained in Step S1, to $V_{LSAW}$(std.calc.) for the standard specimen obtained in Step S4, and to $V_{LSSCW}$(std.calc.) for the standard specimen obtained in Step S9, are obtained. The method can be applied in the same way with respect to the results in FIG. 9. Since these ratios change for each material, reflecting the chemical composition ratios, it is possible to estimate the longitudinal velocity $V_l(f)$, the shear velocity $V_s(f)$, and the density $\rho$, by multiplying the calibrated LSAW velocity $V_{LSAW}$(calibrated), obtained from Step S8 in FIG. 8 relating to the evaluated specimen, or from Step S7 in FIG. 9, or the calibrated LSSCW velocity $V_{LSSCW}$(calibrated), obtained from Step S13 in FIG. 8 or Step S11 in FIG. 9, with the aforementioned acoustic velocity ratios.

As a second evaluation method, since ultra-low-expansion glass materials are generally isotropic solids, it is possible to obtain, as a function of frequency f, an elastic constant $c_{11}$ from the longitudinal velocity $V_l(f)$ estimated with the first evaluation method, an elastic constant $c_{44}$ from the shear velocity $V_s(f)$ estimated above, and an elastic constant $c_{12}$ from the two results, from the following equations.

$$c_{11}(f) = \rho \cdot \{V_l(f)\}^2 \quad (24)$$

$$c_{44}(f) = \rho \cdot \{V_s(f)\}^2 \quad (25)$$

$$c_{12}(f) = c_{11}(f) - 2c_{44}(f) \quad (26)$$

Furthermore, by using the obtained elastic constants, Young's modulus E and Poisson's ratio $\sigma$ indicated as the elastic properties of materials can be obtained as functions of the frequency, as given by the equations below.

$$E(f) = c_{11}(f) - \frac{2\{c_{12}(f)\}^2}{c_{11}(f) + c_{12}(f)} \quad (27)$$

$$\sigma(f) = \frac{c_{12}(f)}{c_{11}(f) + c_{12}(f)} \quad (28)$$

As a third evaluation method, the relationships of the coefficient of thermal expansion and the aforementioned calibrated acoustic properties (calibrated leaky acoustic wave velocities and, estimated on the basis of this, the bulk-wave acoustic velocities, the elastic constants, Young's modulus, and so forth) of the evaluated specimen are found, and the coefficient of thermal expansion is evaluated. Also, the relationships of the results of the chemical composition ratio, the refractive index, etc., and the aforementioned calibrated acoustic properties are obtained, so it is possible to examine the cause of the changes in the acoustic properties of the measured specimen.

Embodiment

Here, as ultra-low-expansion glasses, one piece each of ultra-low-expansion glass #1 (manufactured by Company A), which is $TiO_2$—$SiO_2$ glass, and ultra-low-expansion glass #2 (manufactured by Company B) which is $Li_2O$—$Al_2O_3$—$SiO_2$-system crystallized glass, are taken to be respectively ultra-low-expansion glasses #1-1 and #2-1 and measured with regard to the frequency characteristics of the longitudinal-wave velocity and attenuation coefficient, the shear-wave velocity and attenuation coefficient, and the density, and their temperature dependences in the vicinity of room temperature, and an explanation will be given below for the case that these are taken as standard specimens. Moreover, as a reference, the measurement results for synthetic silica glass #3 (taken to be synthetic silica glass #3-1) (manufactured by Company A), consisting of 100% $SiO_2$, will also be shown (Non-Patent Reference 15).

First, standard specimens are prepared. For the aforementioned three types of standard specimens, the longitudinal-wave and shear-wave acoustic properties were respectively measured in a frequency range from 50 MHz to 250 MHz in the vicinity of 20° C., 23° C., and 26° C. The measurement results at 23° C. are shown in FIGS. 10A to 10F. In this frequency range, synthetic silica glass #3-1 and ultra-low-expansion glass #1-1 have almost no velocity dispersion, so it can be disregarded, but ultra-low-expansion glass #2-1 evidently exhibits velocity dispersion for both longitudinal and shear waves. Also, the attenuation coefficients of ultra-low-expansion glass #2-1 are about one order of magnitude higher than for synthetic silica glass #3-1 and ultra-low-expansion glass #1-1. The shear-wave attenuation coefficients of synthetic silica glass #3-1 and ultra-low-expansion glass #1-1 display very low values; there also arise undulations related to the measurement accuracy, but this is something which originates in the random variation of the acoustic parameters of the salol used in the bonding layer, and undulations of the same extent are also included in the results for ultra-low-expansion glass #2-1.

The attenuation coefficient $\alpha$ can generally be expressed as $\alpha = \alpha_0 f^\beta$. When the results of FIGS. 10D to 10F were approximated with this formula, the results were that $\alpha^l = 1.3 \times 10^{-16}$ $f^2 m^{-1}$ and $\alpha_s = 2.5 \times 10^{-16}$ $f^2 m^{-1}$ for ultra-low-expansion glass #1-1, that $\alpha_l = 9.08 \times 10^{-10}$ $f^{1.36} m^{-1}$ and $\alpha^s = 7.99 \times 10^{-10}$ $f^{1.40} m^{-1}$ for ultra-low-expansion glass #2-1, and that $\alpha_l = 1.1 \times 10^{-16}$ $f^2 m^{-1}$ and $\alpha_s = 2.0 \times 10^{-16}$ $f^2 m^{-1}$ for synthetic silica glass #3-1. The densities were 2197.82 kg/m³ for ultra-low-expansion glass #1-1, 2530.75 kg/m³ for ultra-low-expansion glass #2-1, and 2199.82 kg/m³ for synthetic silica glass #3-1.

Figure 11A:
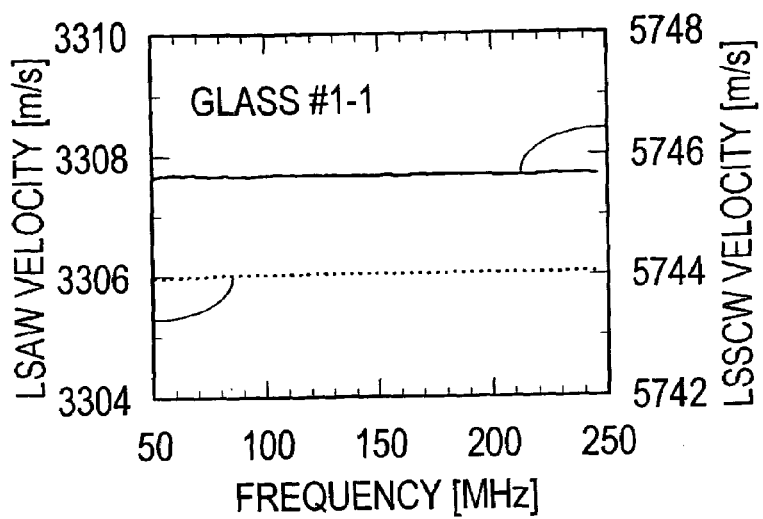
FIG. 11A is a diagram showing the numerically calculated values for leaky acoustic wave velocities with respect to ultra-low-expansion glass #1-1.
Figure 11B:
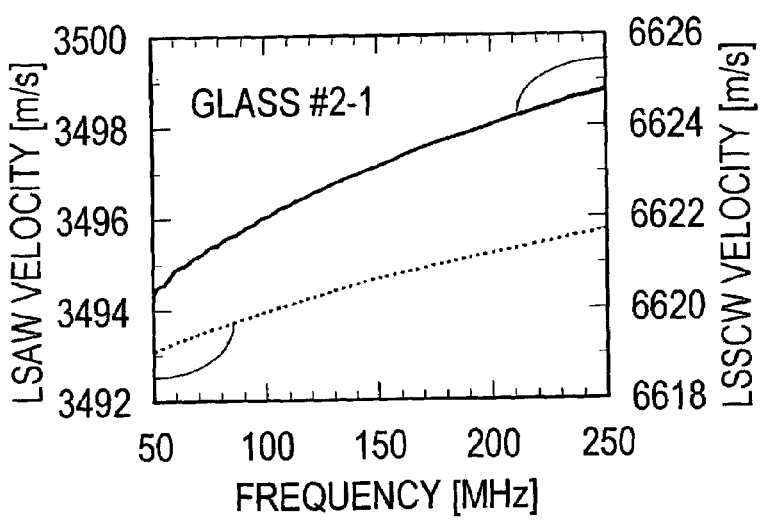
FIG. 11B is a diagram showing the numerically calculated values for leaky acoustic wave velocities with respect to ultra-low-expansion glass #2-1.
Figure 11C:
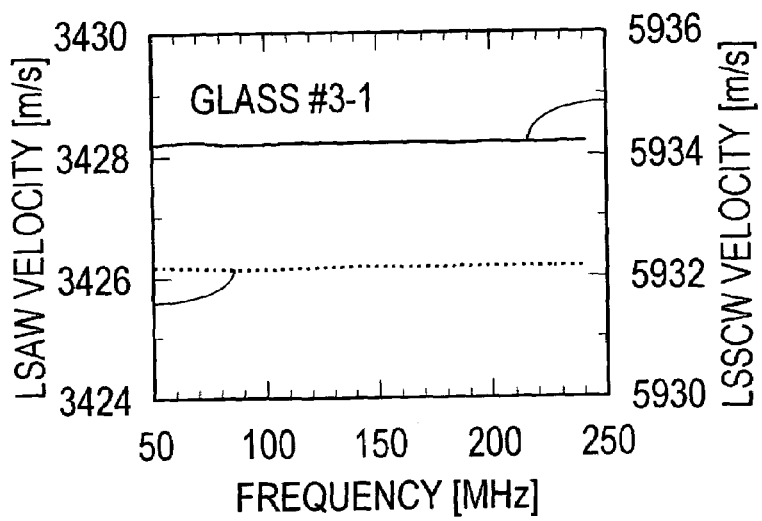
FIG. 11C is a diagram showing the numerically calculated values for leaky acoustic wave velocities with respect to synthetic silica glass #3-1.
Figure 12A:
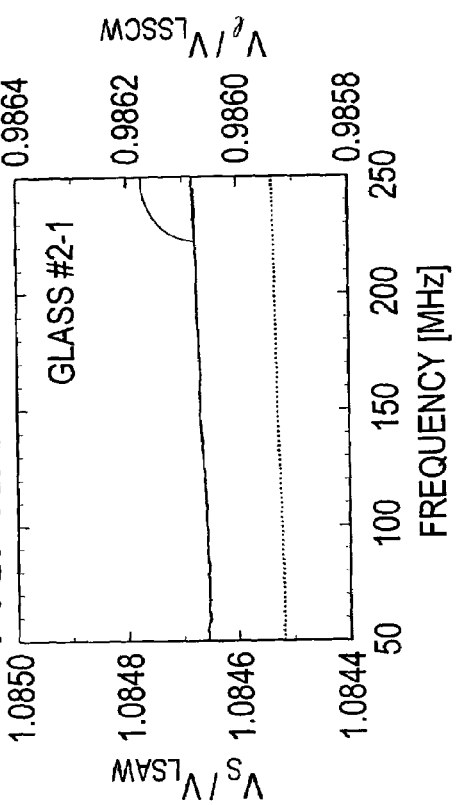
FIG. 12A is a diagram showing the ratio of the shear velocity to the LSAW velocity, and the ratio of the longitudinal velocity to the LSSCW velocity, of ultra-low-expansion glass #1-1, calculated by using the results of FIG. 10A and FIG. 11A.
Figure 12B:
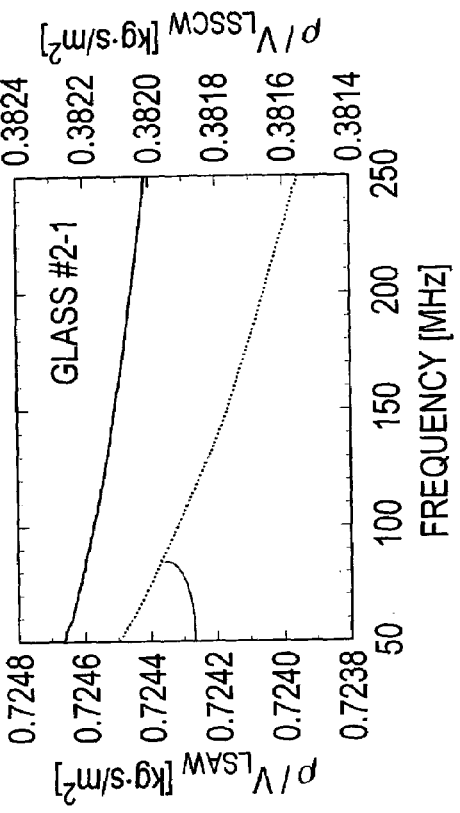
FIG. 12B is a diagram showing the ratios of the density to the LSAW velocity and the LSSCW velocity, obtained from a measured value of the density and the results of FIG. 11A, of ultra-low-expansion glass #1-1.
Figure 12C:
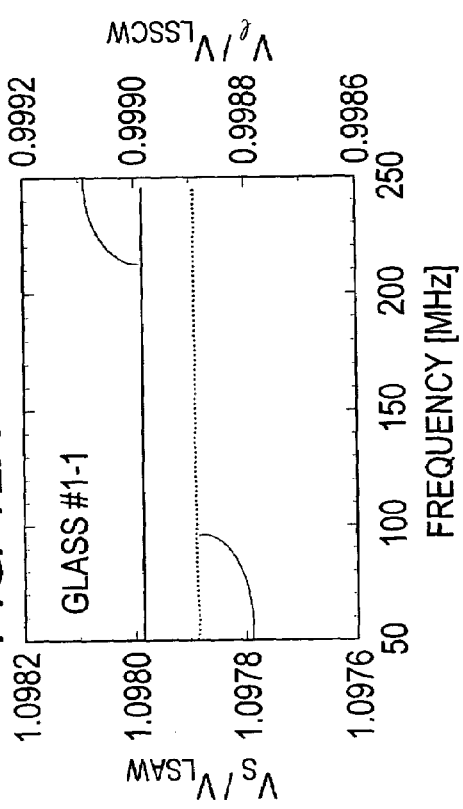
FIG. 12C is a diagram showing the ratios of the shear velocity to the LSAW velocity, and of the longitudinal velocity to the LSSCW velocity, of ultra-low-expansion glass #2-1, calculated by using the results of FIG. 10B and FIG. 11B.
Figure 12D:
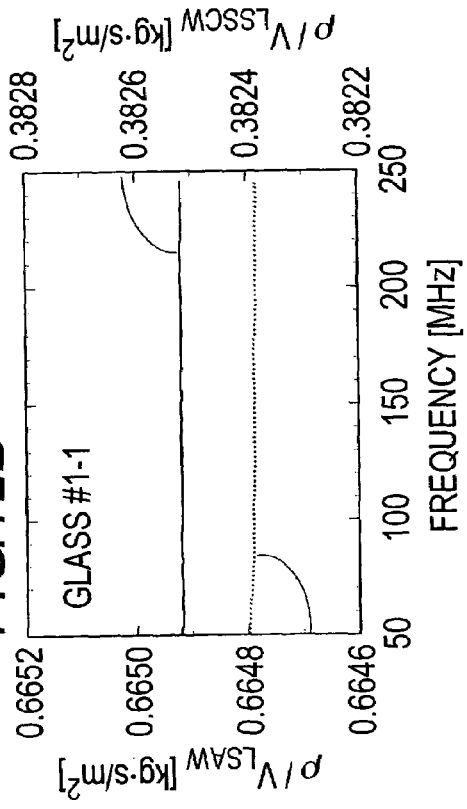
FIG. 12D is a diagram showing the ratios of the density to the LSAW velocity and the LSSCW velocity, obtained from a measured value of the density and the results of FIG. 11B, of ultra-low-expansion glass #2-1.

The results of performing a numerical calculation of the leaky acoustic velocities $V_{LSAW}$ and $V_{LSSCW}$ with Eqs. (8) to (15), using these results, are shown in FIGS. 11A, 11B, and 11C. The ratios $V_s/V_{LSAW}$ of the shear velocity to the LSAW velocity and $V_l/V_{LSSCW}$ of the longitudinal velocity to the LSSCW velocity of ultra-low-expansion glass #1-1, obtained from FIG. 10A and FIG. 11A, are shown in FIG. 12A. At 225 MHz, the ratio of the shear velocity to the LSAW velocity is 1.0979, and the ratio of the longitudinal velocity to the LSSCW velocity is 0.9990. Also, the ratios $\rho/V_{LSAW}$ and $\rho/V_{LSSCW}$ of the density to the LSAW velocity and to the LSSCW velocity, obtained from measured densities and the results of FIG. 11A, are as shown in FIG. 12B. Similarly, for ultra-low-expansion glass #2-1, each velocity ratio is shown in FIG. 12C, and the density-to-velocity ratio is shown in FIG. 12D. At 225 MHz, the ratio of the shear velocity to the LSAW velocity is 1.0845, and the ratio of the longitudinal velocity to the LSSCW velocity is 0.9861.

Figure 13A:
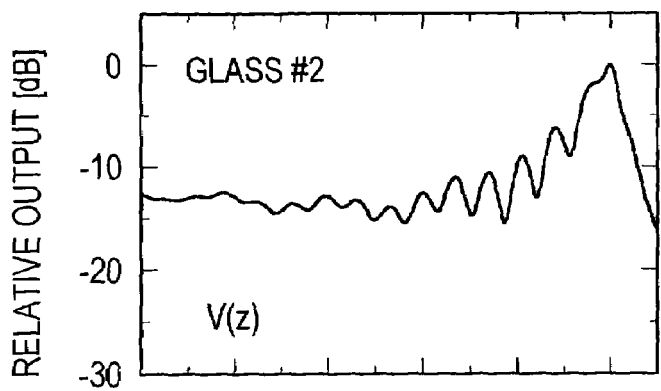
FIG. 13A is a diagram showing the V(z) curve measured at f=225 MHz for ultra-low-expansion glass #2.
Figure 13B:
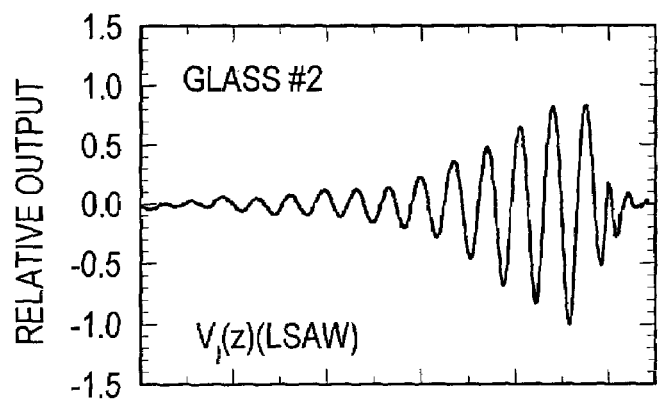
FIG. 13B is a diagram showing the $V_I(z)$ curve for LSAW.
Figure 13C:
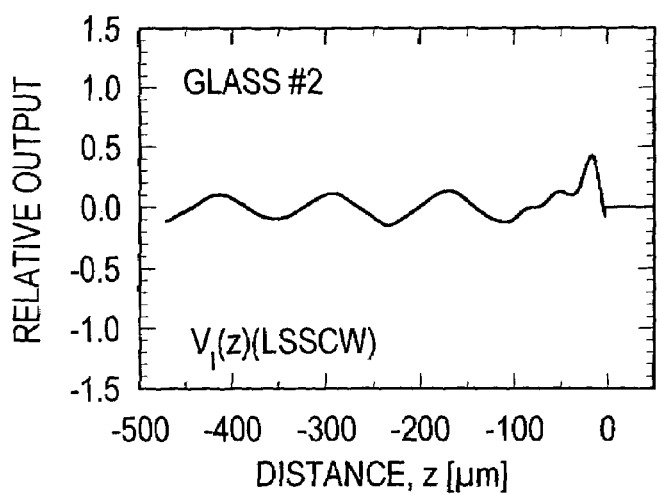
FIG. 13C is a diagram showing the $V_I(z)$ curve for LSSCW.

Measurement examples of the V(z) curve, the $V_l(z)$ (LSAW) curve, and the $V_l(z)$(LSSCW) curve for ultra-low-expansion glass #2 at 225 MHz are shown in FIGS. 13A, 13B, and 13C. Ultra-low-expansion glass #2 has a smaller $\alpha_{LSAW}$ than ultra-low-expansion glass #1, and the range in which an interference waveform in FIG. 13B is present is wider than in the case in FIG. 4B. The results of performing a chemical analysis by the fluorescent X-ray analysis method with respect to the three types of glass #1-1, glass #2-1, and glass #3-1 are shown in FIG. 14. However, as for the $Li_2O$ concentration of ultra-low-expansion glass #2-1, the value of Non-Patent Reference 16 has been used. The acoustic properties of each specimen differ, reflecting the differences in chemical composition ratios. Also, as far as ultra-low-expansion glass #2-1 is concerned, crystallization technology is used in order to implement an ultra-low coefficient of thermal expansion, and, in addition to the chemical composition ratios, changes in the acoustic properties originating in this manufacturing process are added.

Changes in acoustic velocity are due to changes in the elastic constants and changes in the density. The elastic constants $c_{11}$ and $c_{44}$, obtained by Eqs. (24) and (25) from the longitudinal and shear velocities at 225 MHz, and the densities for ultra-low-expansion glass #1-1 and synthetic silica glass #3-1, are shown in FIG. 15. The changes in $c_{11}$ and $c_{44}$ are 70 times and 80 times greater, respectively, than the changes in the density. It can be said that the changes in acoustic velocity are mainly due to changes in the elastic constants.

Due to changes in the quantity of chemical compositions of glasses, various physical quantities (physical constants)

change. For example, the quantity of change in a certain physical quantity or a chemical quantity when there is a unit change in the LSAW velocity is defined as the LSAW velocity sensitivity for that physical quantity or chemical quantity. If the coefficients of thermal expansion and the LSAW velocities of glasses A and B which have differences in the quantity of chemical compositions are respectively taken to be $CTE_A$ and $V_{LSAWA}$ for glass A and $CTE_B$ and $V_{LSAWB}$ for glass B, the LSAW velocity sensitivity for the coefficient of thermal expansion is expressed as $(CTE_A-CTE_B)/(V_{LSAWA}-V_{LSAWB})$, and the resolution is obtained by multiplying this sensitivity with the resolution of the LSAW velocity. In a similar way, the LSAW velocity sensitivities and resolutions for the density, the concentration of a specific chemical component (e.g. $TiO_2$), or another physical quantity can be defined, and, also, the LSSCW velocity sensitivity and resolution for an arbitrary physical quantity can be defined.

From FIG. 14, it can be seen that only $SiO_2$ and $TiO_2$ are included in ultra-low-expansion glass #1-1, the $TiO_2$ concentration being 6.9 wt %. From a comparison of the leaky acoustic wave velocities (FIGS. 11A and 11C) of ultra-low-expansion glass #1-1 and synthetic silica glass #3-1 (manufactured by Company A), which is glass composed of 100% $SiO_2$, the LSAW velocity and LSSCW velocity sensitivities and resolutions for the $TiO_2$ concentration, the coefficient of thermal expansion, and the density were respectively obtained as shown in FIG. 16 and FIG. 17. Here, the coefficient of thermal expansion of ultra-low-expansion glass #1-1 was assumed to be 0 ppb/K, and for synthetic silica glass #3-1, it was taken to be 520 ppb/K, a catalog value. It is the LSAW velocity that offers a higher sensitivity and resolution than the LSSCW velocity for those characteristics, so it is the LSAW velocity that is suited to the analysis and evaluation of materials. In order to satisfy the specification of ±5 ppb/K set as a target for ultra-low-expansion glass for EUVL use, it follows, since 5/4.33=1.15, that the variation in the LSAW velocity of $TiO_2$—$SiO_2$ glass should be within ±1.15 m/s.

Figure 19A:
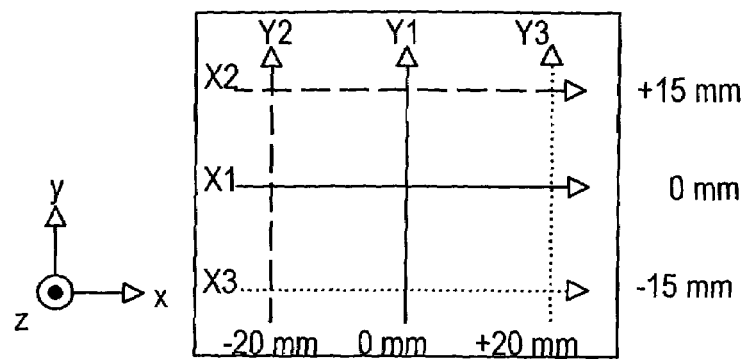
FIG. 19A is a diagram showing the LSAW velocity measurement positions for ultra-low-expansion glass specimen #1-2, for which the periodic striae are parallel to the surface of the specimen.
Figure 19B:
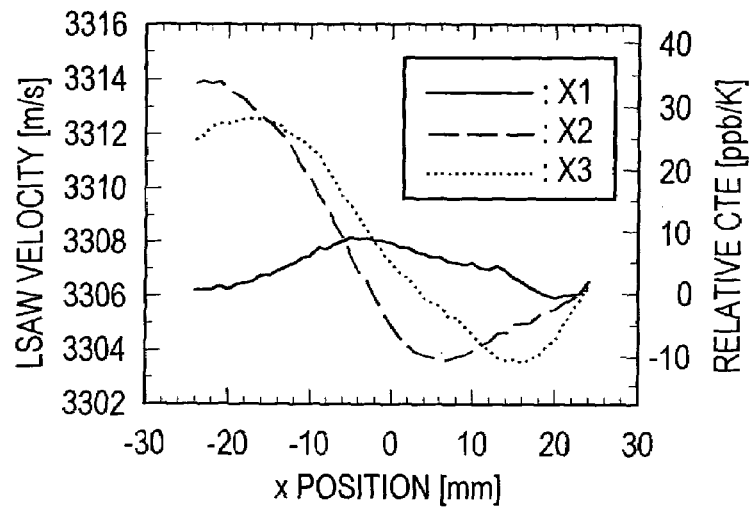
FIG. 19B is a diagram showing the measurement results for the LSAW velocity with respect to the measurement lines X1, X2, and X3 in FIG. 19A.
Figure 19C:
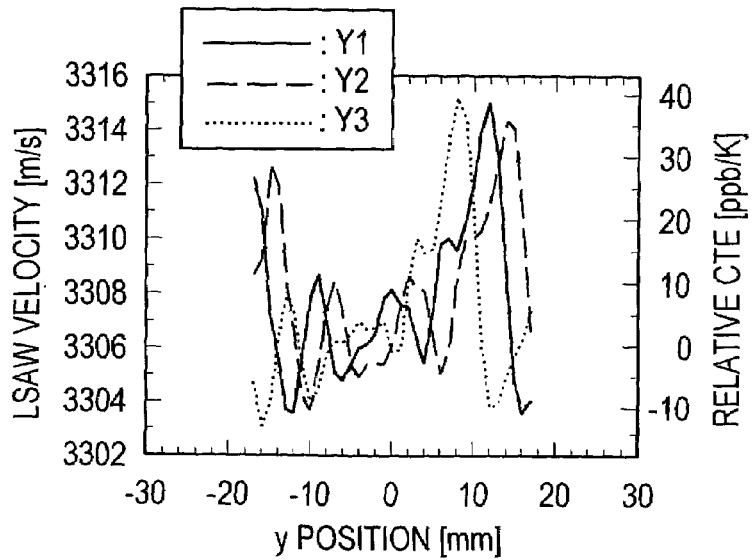
FIG. 19C is a diagram showing the measurement results for the LSAW velocity with respect to the measurement lines Y1, Y2, and Y3 in FIG. 19A.

Next, the LFB ultrasonic material characterization system is applied to the evaluation of ultra-low-expansion glass #1 (manufactured by Company A), a commercially available $TiO_2$—$SiO_2$ glass. From a Grade-1 glass ingot 10 (coefficient of thermal expansion (5–35° C.): within 0±30 ppb/K, distribution in a glass ingot: 10 ppb/K) as shown in FIG. 18A, one each of a specimen for which periodic striae 11 are parallel to the surface of the glass substrate 12 (specimen #1-2), as shown in FIG. 18B, and a specimen for which periodic striae 11 are perpendicular to the surface of the glass substrate 12 (specimen #1-3), as shown in FIG. 18C, were prepared. The substrate dimensions are 50 mm×60 mm×4.7 mm$^t$. For specimen #1-2 (FIG. 18B), measurements of the LSAW velocity were performed at intervals of 1 mm at an ultrasonic frequency f=225 MHz along the measurement lines shown in FIG. 19A. The LSAW propagation direction is parallel to the direction of each measurement line. The LSAW velocity measurement results are shown in FIG. 19B and FIG. 19C. Across the surface of the specimen, a maximum velocity variation of 12.14 m/s was captured. From FIG. 16, this change in acoustic velocity is converted into a change of 52.6 ppb/K in the coefficient of thermal expansion, a change of 0.70 wt % in the $TiO_2$ concentration, and a change of 0.203 kg/m$^3$ in the density. This is five times greater than the specification for the coefficient of thermal expansion (within 10 ppb/K in a glass ingot).

Figure 20A:
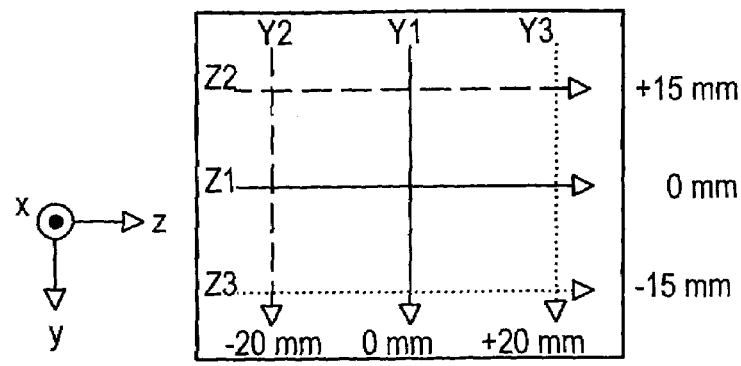
FIG. 20A is a diagram showing the LSAW velocity measurement positions for ultra-low-expansion glass specimen #1-3, for which the periodic striae are perpendicular to the surface of the specimen.
Figure 20B:
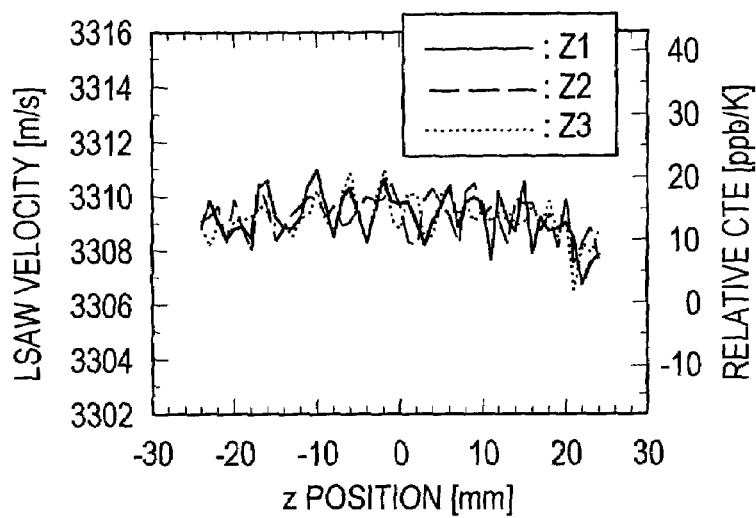
FIG. 20B is a diagram showing the measurement results for the LSAW velocity with respect to the measurement lines Z1, Z2, and Z3 in FIG. 20A.
Figure 20C:
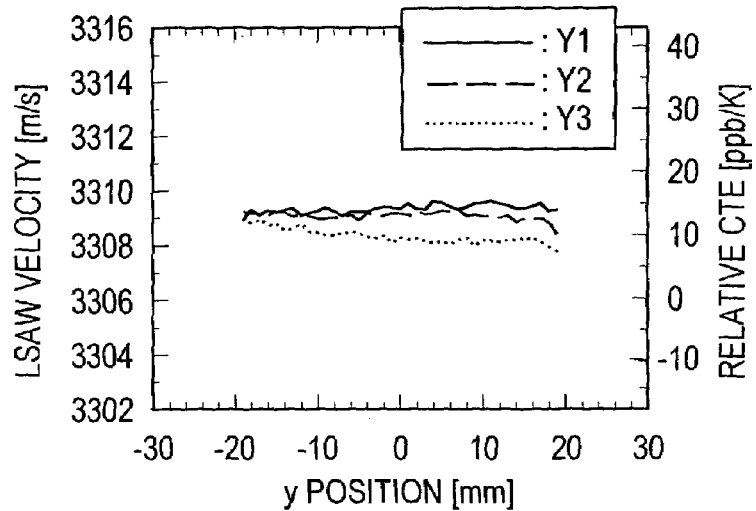
FIG. 20C is a diagram showing the measurement results for the LSAW velocity with respect to the measurement lines Y1, Y2, and Y3 in FIG. 20A.

Similarly, for specimen #1-3 (FIG. 18C), the results of measurements of the LSAW velocity performed along the measurement lines shown in FIG. 20A are shown in FIG. 20B and FIG. 20C. Across the surface of the specimen, a maximum velocity variation of 4.34 m/s was captured. Fine periodic velocity variations can be observed in the z direction, but they cannot be observed in the y direction.

Figure 21A:
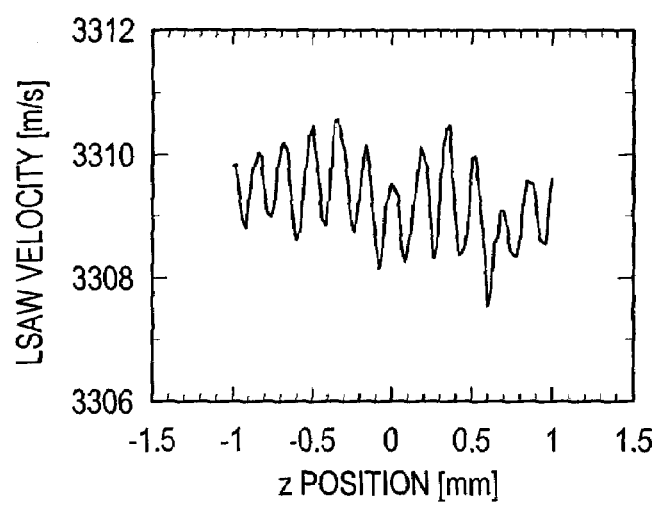
FIG. 21A is a diagram showing the results of measurements at intervals of 0.02 mm in the z direction (FIG. 18C) in a range of ±1 mm from the specimen center, with respect to ultra-low-expansion glass specimen #1-3 for which periodic striae are perpendicular to the surface of the specimen.
Figure 21B:
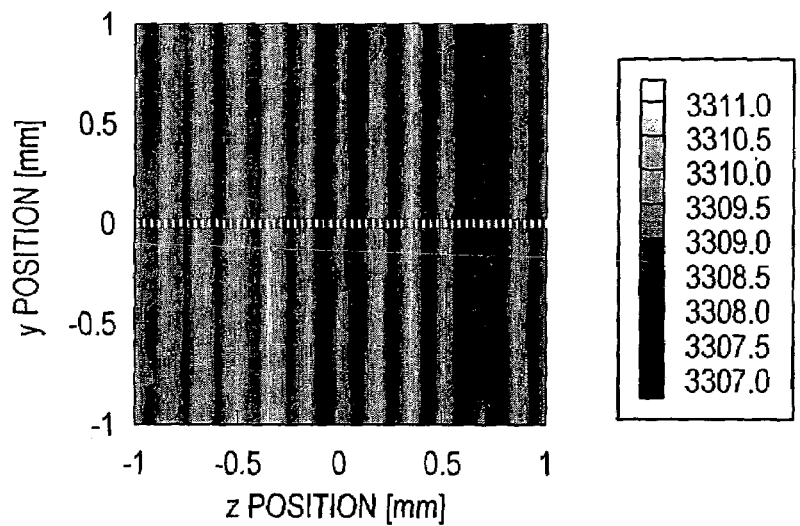
FIG. 21B is a diagram showing the results of performing measurements with a two-dimensional distribution in a 2 mm×2 mm region in the vicinity of the specimen center, at intervals of 0.05 mm in the z direction (FIG. 18C) and at intervals of 0.25 mm in the y direction.

The results of measuring LSAW velocities for the z-axis propagation, in order to capture changes due to striae, at 0.02-mm intervals in the z direction in a range of ±1 mm from the specimen center are shown in FIG. 21A, and the results of performing measurements with a two-dimensional distribution for an area of 1 mm×1 mm in the vicinity of the specimen center at intervals of 0.05 mm in the z direction and 0.25 mm in the y direction are shown in FIG. 21B. In FIG. 21B, the magnitude of the velocity is associated with shades of grey and the white dotted line corresponds to the measurement positions in FIG. 21A. A periodicity of approximately 0.17 mm was observed in the z direction. From this result and FIG. 16, it follows that layers poor in $TiO_2$ having a high acoustic velocity and layers rich in $TiO_2$ having a low acoustic velocity are manifested alternately.

Figure 1:
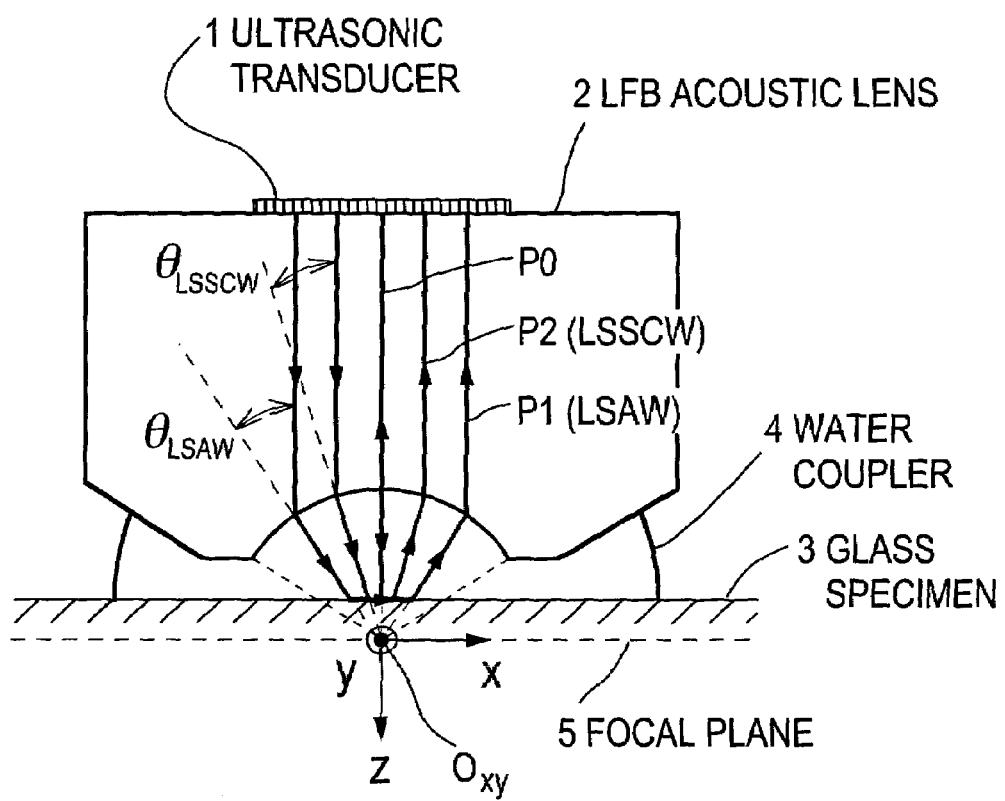
FIG. 1 is a schematic diagram for explaining the principle of generation of a V(z) curve.

The difference in the acoustic velocity variations of 12.14 m/s for specimen #1-2 and 4.34 m/s for specimen #1-3 is something which is related to the measurement region of the LFB ultrasonic device employed here and the periodicity of the change in the elastic characteristics. The measurement region (W×D) depends on the LSAW propagation distance W related to the defocus distance z (the distance between the focal point Oxy and the surface of specimen 3 in FIG. 1) in the focused direction and is given by $2|z|\tan\theta_{LSAW}$, and depends on the width of the ultrasonic beam, D, in the unfocused direction. Since the maximum defocus distance z used in the measurement and analysis with respect to ultra-low-expansion glasses is −280 µm, it can be considered that the maximum LSAW propagation distance in the focused direction in the measurement region is about 280 µm. Moreover, the effective beam width in the unfocused direction of the ultrasonic device designed for the 200-MHz range used in the measurements can be considered to be 900 µm. The resolution in the depth direction of the substrate is approximately one wavelength (approximately 15 µm at 225 MHz) below the substrate surface where the LSAW energy is concentrated.

Figure 22A:
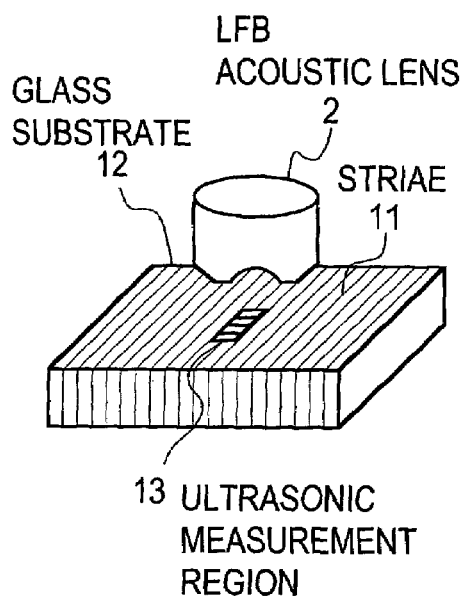
FIG. 22A is a diagram showing, for the specimen prepared perpendicular to the periodic striae as shown in FIG. 18C, the ultrasonic measurement region when the focused direction of an ultrasonic focused beam formed by an LFB acoustic lens is perpendicular to the striae plane.
Figure 22B:
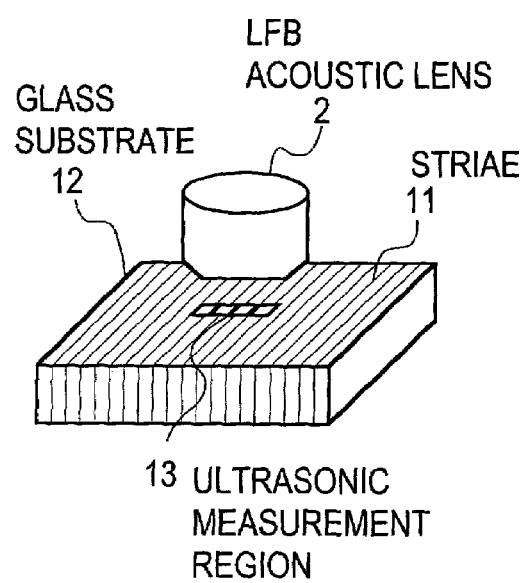
FIG. 22B is a diagram showing the ultrasonic measurement region when that direction is parallel to the striae plane.

As a reason why specimen #1-2 (FIG. 18B) has a larger velocity distribution compared to specimen #1-3 (FIG. 18C), it can be considered that, since the striae plane are not completely flat but curved over the surface of the specimen substrate although the specimen #1-2 was prepared parallel to the striae plane, it is something which captures the distribution of elastic characteristics related to the periodic striae, the maximum variation being 12.14 m/s. In the case that specimen #1-3 (FIG. 18C) is scanned in the z direction along which LSAWs propagate, the relationship between an ultrasonic measurement region 13 and the periodicity of striae 11 is as shown in FIG. 22A, and since the LSAW propagation distance (maximum 280 µm at z=−280 µm) of the short side of ultrasonic measurement region 13 becomes greater than the periodicity of striae 11 (170 µm), the surface characteristics over the striae layers are averaged, so that the velocity changes become smaller. Further, in the case of a scan in the y direction along which LSAWs propagate, the situation is as shown in FIG. 22B. Since the effective ultrasonic beam width (900 µm) in the unfocused direction in the measurement region is approximately five times greater than the periodicity of the striae, the LSAW velocities are measured as the averaged values of their characteristics, so the changes in LSAW velocity become much smaller. Also, by imaging the striae as in FIG. 21B, it is also possible to accurately evaluate the direction of the striae with respect to the surface of the specimen.

Figure 22C:
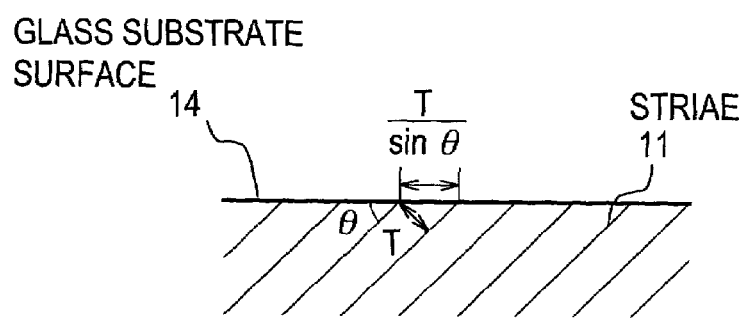
FIG. 22C is a diagram indicating the striae periodicity at the specimen surface when the striae plane are inclined at an angle θ with respect to the substrate surface.

Next, an investigation will be carried out regarding a method of capturing the changes in the true acoustic properties due to the striae. As was shown in FIG. 21A and FIG. 21B, the striae are present in a periodic manner. If the substrate is cut obliquely with respect to the striae plane, the apparent periodicity of striae 11 on a glass substrate surface 14 is expressed as T/sin θ where T is the periodicity of the striae, as shown in FIG. 22C. The smaller θ is, the greater the apparent periodicity of the striae on the substrate surface becomes; if T is taken to be 170 µm, the apparent periodicity of the striae on the substrate surface is, for example, 170 µm when θ=90°, 340 µm when θ=30°, 1 mm when θ=9.8°, 2 mm when θ=4.9°, and becomes infinitely great when θ=0°. By choosing an appropriate cut angle of the substrate surface to the striae plane, so as to have an apparent periodicity of the striae sufficiently greater than the maximum LFB propagation distance of the ultrasonic beam used (here, 280 µm), it is possible to capture the change in the true acoustic properties due to the striae.

Figure 23A:
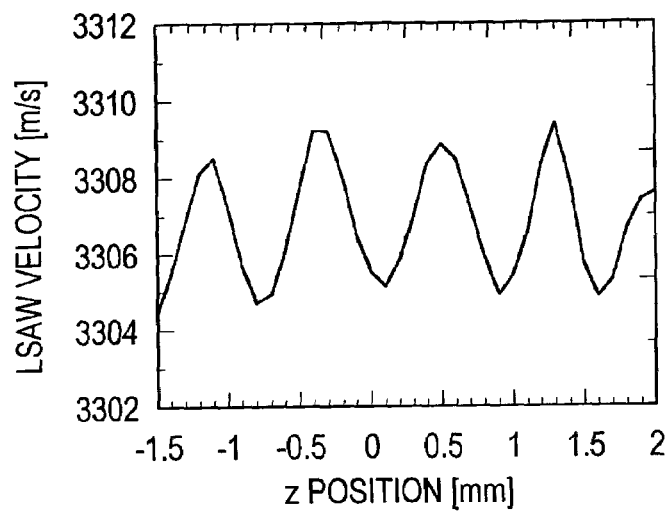
FIG. 23A is a diagram showing the measured results in the vicinity of the specimen center, at intervals of 0.1 mm in the z direction, for a specimen wherein the periodic striae are inclined at an angle of 12° with respect to the face of the specimen.
Figure 23B:
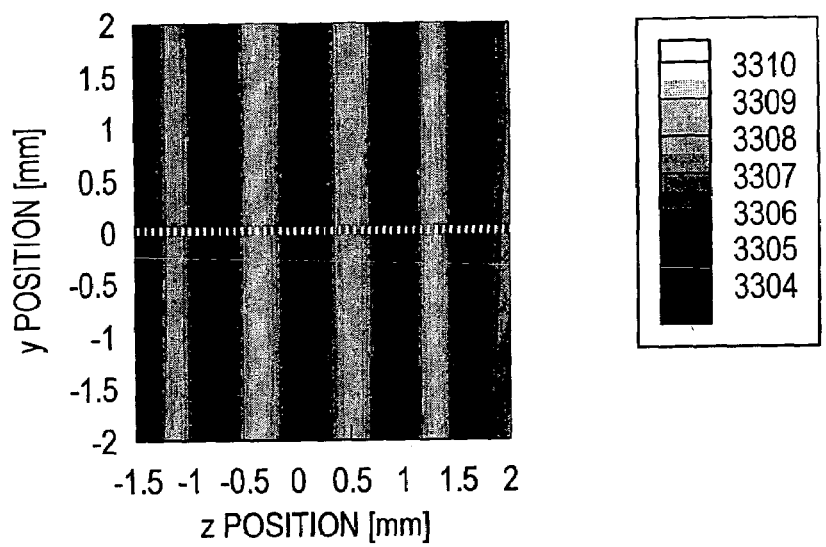
FIG. 23B is a diagram showing the results of performing measurements with a two-dimensional distribution in a region in the vicinity of the specimen center, at intervals of 0.1 mm in the z direction and at intervals of 1 mm in the y direction.

As an example, another specimen is prepared wherein the striae plane are inclined at an angle of 12° with respect to the surface of the substrate, and the results of measuring LSAW velocities for the z-axis propagation at intervals of 0.1 mm along the z direction are shown in FIG. 23A and the results of performing measurements with a two-dimensional distribution in a region of 3.5 mm×4 mm, at intervals of 0.1 mm along the z direction and at intervals of 1 mm along the y direction, are shown in FIG. 23B as shades of grey corresponding to the magnitudes of the LSAW velocity. The maximum velocity difference was 5.21 m/s, so the apparent periodicity was approximately 0.8 mm. If this velocity difference is converted, by using the sensitivity shown in FIG. 16, into changes in other physical/chemical properties, it corresponds to changes of 22.6 ppb/K in the coefficient of thermal expansion, 0.30 wt % in the $TiO_2$ concentration, and 0.087 kg/m³ in the density.

Figure 24:
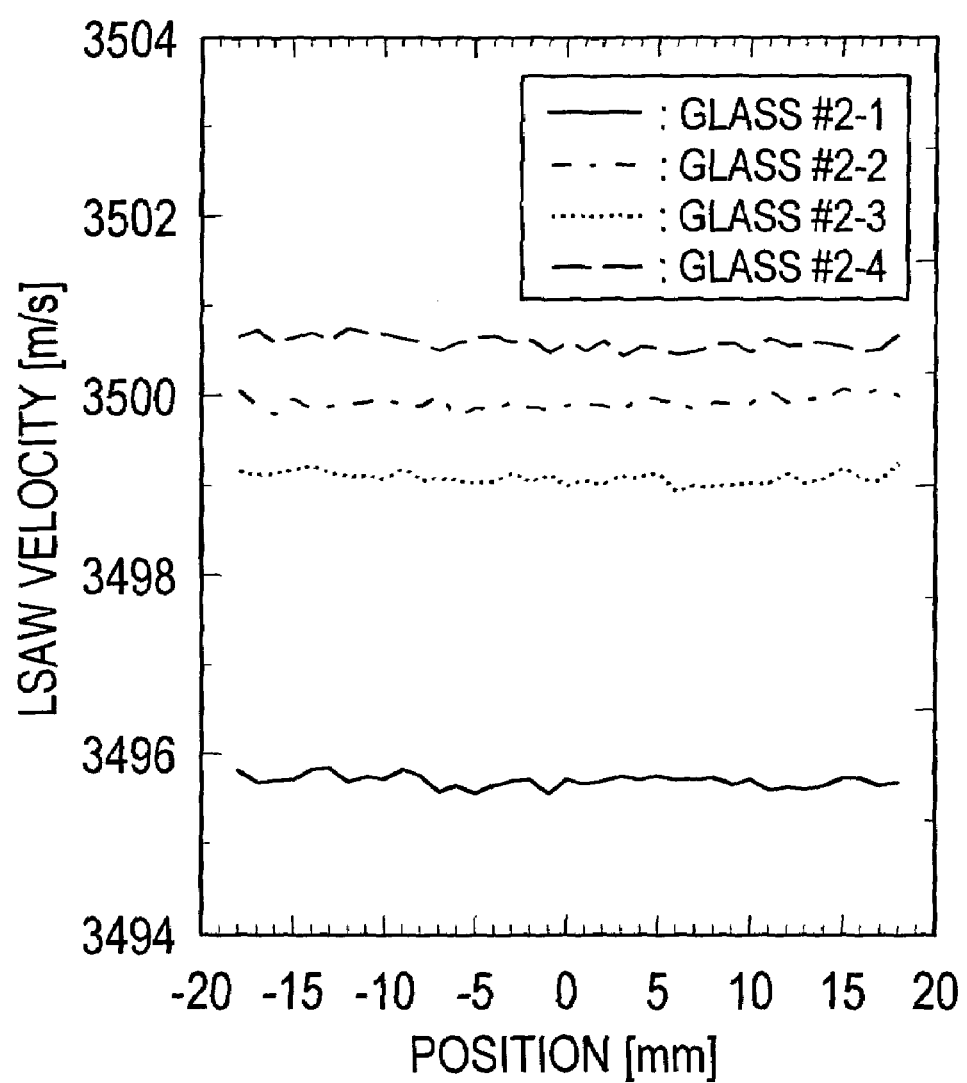
FIG. 24 is a diagram showing the distributions of the LSAW velocity for ultra-low-expansion glasses #2.

Next, an application was made to ultra-low-expansion glass #2. As specimens, a total of four specimens with dimensions of 50 mm×50 mm×5.5 mm' were picked out, one each from four different ingots (two from Class 1 (of these, one is taken to be #2-1 and the other #2-2), one from Class 2 (taken to be #2-3), and one from Class 3 (taken to be #2-4)). Here, the specifications for the absolute values of the coefficients of thermal expansion (0–50° C.) of the respective classes were within 0±20 ppb/K for Class 1, within 0±50 ppb/K for Class 2, and within 0±100 ppb/K for Class 3, and the specification for the relative change inside an ingot was within ±20 ppb/K for the three. The results of performing, for each specimen, measurements of the LSAW velocity distribution in one direction, including the center, are shown in FIG. 24. The velocity distribution in one substrate was at most 0.32 m/s, which is quite low. There existed significant variations in the LSAW velocities among the ingots, a maximum of 5.21 m/s being captured among the four specimens. In particular, a great difference of 4.53 m/s was detected between specimens #2-1 and #2-2 in the highest-grade Class 1. Moreover, the results of obtaining the chemical composition ratios by the X-ray fluorescence analysis method and the densities are shown in FIG. 25 and FIG. 26, respectively. The changes in the acoustic properties are something that reflects the changes in chemical composition ratios and differences in the crystallization processes.

Figure 4A:
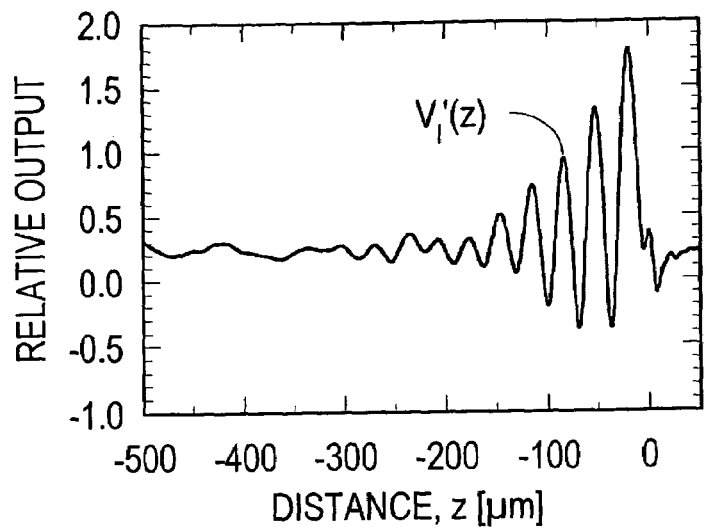
FIG. 4A is a diagram showing the curve obtained by subtracting the $V_L'(z)$ curve from the V(z) curve.
Figure 4B:
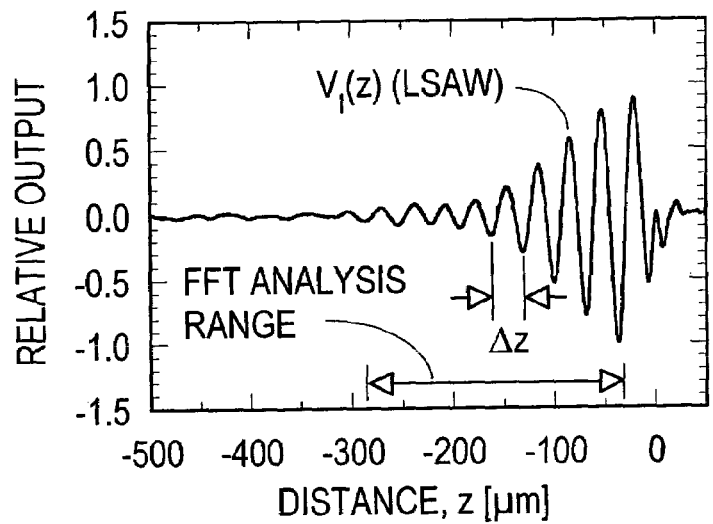
FIG. 4B is a diagram showing a $V_I(z)$ curve for LSAW.
Figure 4C:
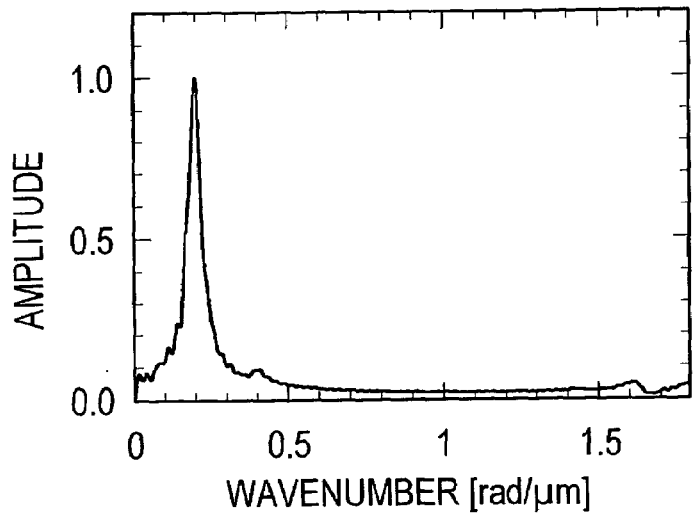
FIG. 4C is a diagram showing the wavenumber spectrum distribution obtained by making an FFT analysis of the $V_I(z)$ curve for LSAW.
Figure 5A:
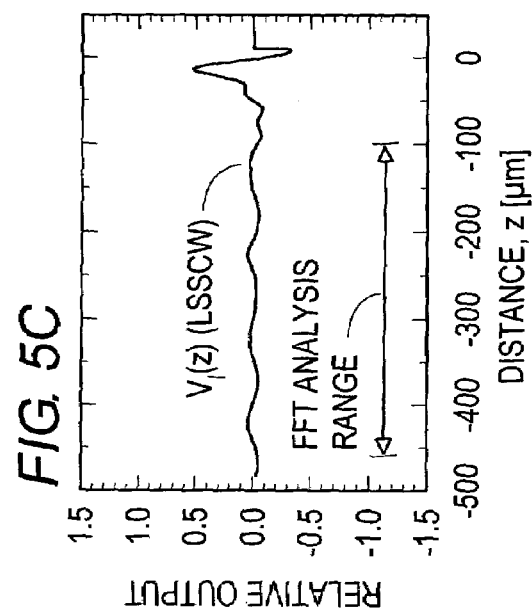
FIG. 5A is a diagram showing the low-frequency component extracted from FIG. 4A.
Figure 5C:
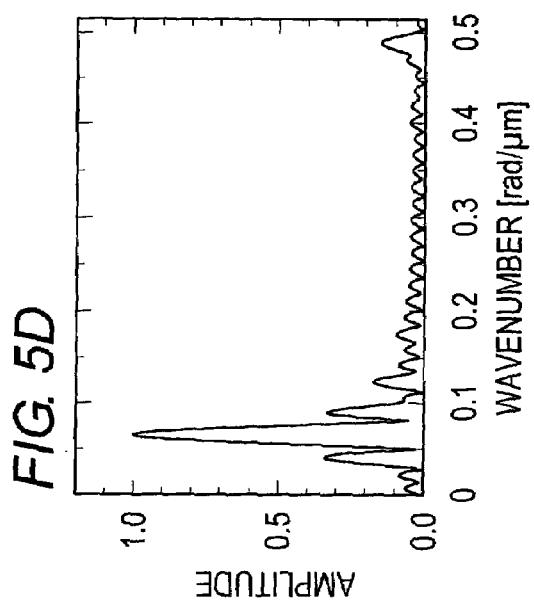
FIG. 5C is a diagram showing a $V_I(z)$ curve for LSSCW.
Figure 5B:
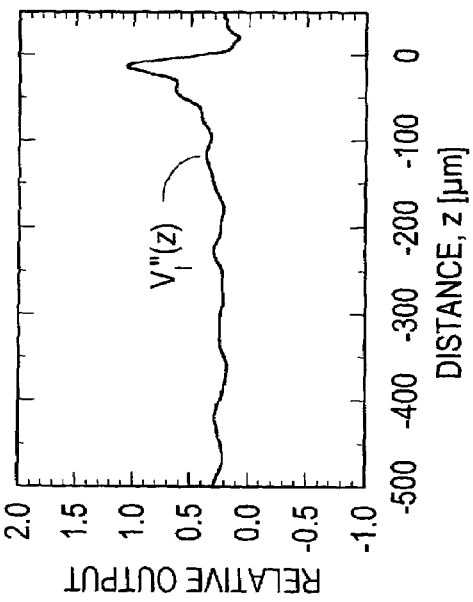
FIG. 5B is a diagram showing the $\Delta V_L(z)$ curve.
Figure 5D:
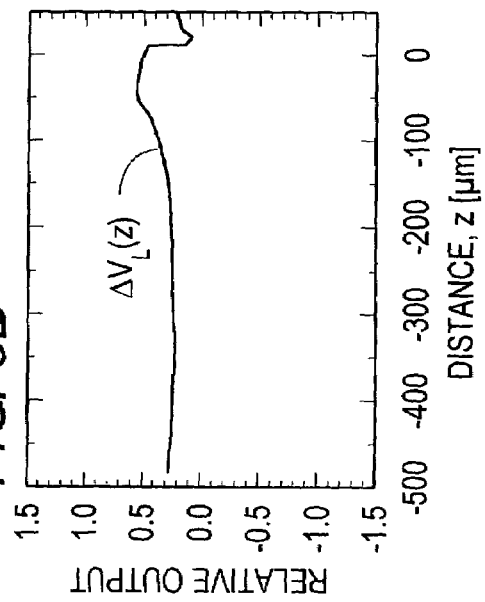
FIG. 5D is a diagram showing the wavenumber spectrum distribution obtained by making an FFT analysis of the $V_I(z)$ curve for LSSCW.

Next, an investigation regarding an improvement in the measurement accuracy (resolution, and consequently, reproducibility) of the LSAW velocity is conducted. As shown in FIG. 16, the reproducibility (±σ) of the LSAW velocity for ultra-low-expansion glass #1 was ±0.09 m/s (±0.0026%) which is worse than the ±0.0018% value for ultra-low-expansion glass #2, or the ±0.0007% value for single crystal materials like Gadolinium Gallium Garnet (GGG) or $LiTaO_3$. The V(z) curve for ultra-low-expansion glass #1 has a high waveform attenuation factor and the analysis region that can be used for LSAW analysis goes as far as −280 µm, as shown in FIG. 4B. Moreover, as to ultra-low-expansion glass #2, the analysis region goes as far as −480 µm, as shown in FIG. 13B, and for single crystal materials, interference waveform is present in all regions of the measurement range and can be used for analysis. Due to this, the waveform attenuation factor $\alpha_0$ of the $V_f(z)$(LSAW) curve shown in FIG. 4B should be reduced and the analysis region should be widened, in order to improve the reproducibility of the LSAW velocity.

The factor $\alpha_{LSAW}$ in the V(z) curve analysis method is obtained from the equation below (Non-Patent Reference 5).

$$\alpha_{LSAW} = \frac{\alpha_0 \cos\theta_{LSAW} + 2\alpha_W}{2k_{LSAW}\sin\theta_{LSAW}} \quad (29)$$

where $k_{LSAW}$ is the LSAW wavenumber. Generally, $\alpha_{LSAW}$ is expressed as mentioned below, as a sum of an attenuation factor $\alpha_{WL}(LSAW)$ accompanying longitudinal-wave radiation in water, a factor $\alpha_{AB}(LSAW)$ of absorption of acoustic waves in the solid, and a scattering attenuation factor $\alpha_{SC}(LSAW)$.

$$\alpha_{LSAW} = \alpha_{WL}(LSAW) + \alpha_{AB}(LSAW) + \alpha_{SC}(LSAW) \quad (30)$$

Here, if one assumes, because of optical polishing of the specimen surface, that there is neither scattering at the boundary interface between the water and the specimen nor scattering resulting from the internal specimen structure, $\alpha_{SC}$ can be disregarded.

From Eq. (29), $\alpha_0$ is expressed with the following equation.

$$\alpha_0 = \frac{2k_{LSAW}\sin\theta_{LSAW}\alpha_{LSAW} - 2\alpha_W}{\cos\theta_{LSAW}} \quad (31)$$

If Eq. (30) is substituted in Eq. (31), taking $\alpha_{SC}(LSAW) = 0$, the following equation is obtained:

$$\alpha_0 = 2k_{LSAW}\tan\theta_{LSAW}\alpha_{WL}(LSAW) + \\ 2k_{LSAW}\tan\theta_{LSAW}\alpha_{AB}(LSAW) - \frac{2\alpha_W}{\cos\theta_{LSAW}} \quad (32)$$

The LSAW particle displacement components are composed of longitudinal-wave and shear-wave displacement components, but the shear-wave component is the main one and, as is moreover revealed from the results of FIG. 10, the attenuation for the shear waves is higher. Consequently, if it is assumed that the LSAW term of absorption inside the solid is equal to the shear-wave attenuation coefficient as and that $\alpha_{AB}(LSAW) = \alpha_s/k_{LSAW}$, Eq. (32) is rewritten as a function of the ultrasonic frequency f, like $\alpha_s = \alpha_{s0}f^\beta$, $\alpha_W = \alpha_{W0}f^2$, and $k_{LSAW} = 2\pi f/V_{LSAW}$, and the following equation is obtained.

$$\alpha_0 = \tag{33}$$
$$\frac{4\pi}{V_{LSAW}}\tan\theta_{LSAW}\alpha_{WL}(LSAW)\cdot f + 2\tan\theta_{LSAW}\alpha_{S0}\cdot f^\beta - \frac{2\alpha_{W0}}{\cos\theta_{LSAW}}\cdot f^2$$

Figure 27A:
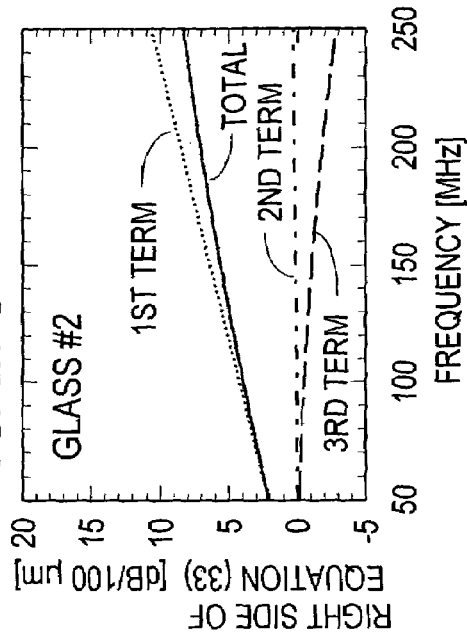
FIG. 27A is a diagram showing the changes in each term on the right side of Eq. (33), related to the waveform attenuation factor of the $V_f(z)$ curve with respect to LSAW of ultra-low-expansion glass #1.

The results of calculating $\alpha_0$ from Eq. (33) for the standard specimens, ultra-low-expansion glass #1 and ultra-low-expansion glass #2, are shown in FIG. 27A and FIG. 27C. Here, the dotted lines, the dash and dot lines, and the dashed lines represent the calculated results of the first, second, and third terms of Eq. (33), respectively, and the solid lines represent the sum $\alpha_0$. Here, the approximated curve ($\alpha_s=2.5\times10^{-16}$ $f^2m^{-1}$) for the shear wave attenuation coefficient was used as $\alpha_{AB}$. The factor $\alpha_0$ increases as the frequency becomes higher. In this case, the predominant factor determining $\alpha_0$ is the attenuation due to radiation to water, calculated with the $\alpha_{WL}$(LSAW) term.

Figure 27B:
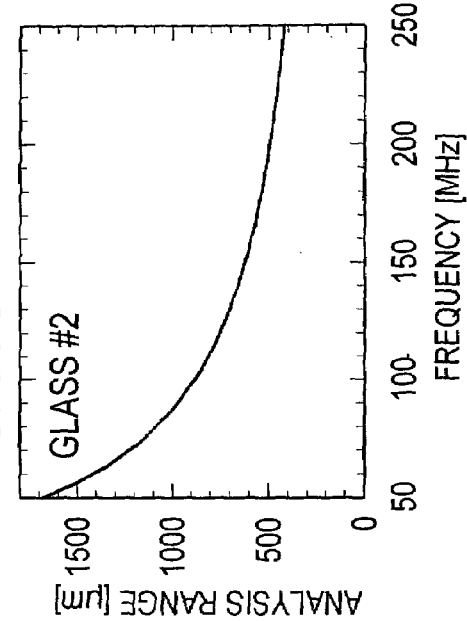
FIG. 27B is a diagram showing the analysis region for the analysis of ultra-low-expansion glass #1.
Figure 27C:
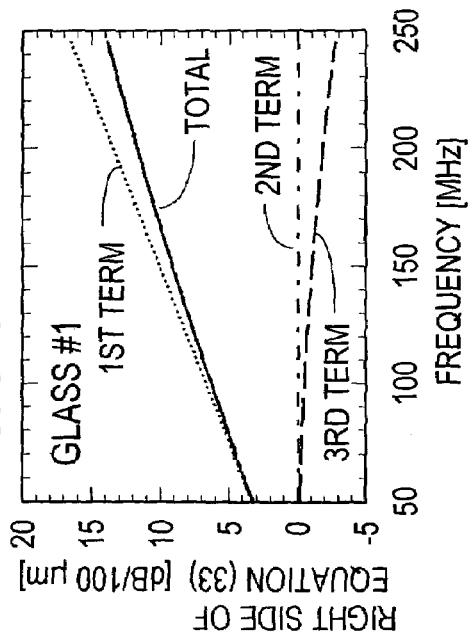
FIG. 27C is a diagram showing the changes in each term on the right side of Eq. (33), related to the waveform attenuation factor of the $V_f(z)$ curve with respect to LSAW of ultra-low-expansion glass #2.
Figure 27D:
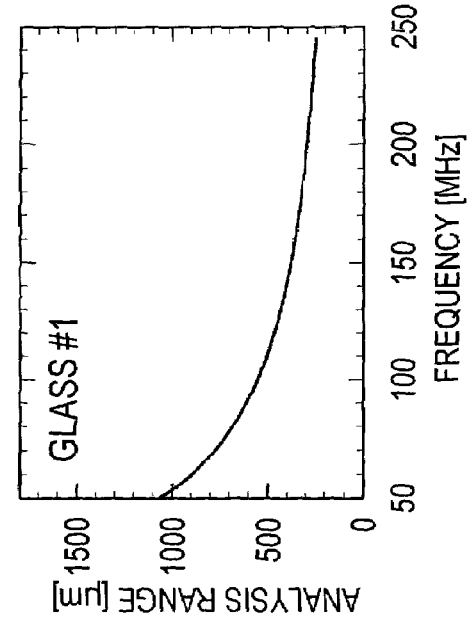
FIG. 27D is a diagram showing the analysis region for the analysis of ultra-low-expansion glass #2.

Next, using the results of FIG. 27A and FIG. 27C, the results of calculating the distances from the focal points, which can be used in normal V(z) curve analysis, up to points with 35-dB attenuation are shown in FIG. 27B and FIG. 27D. In both results, the distance up to the point with 35-dB attenuation becomes shorter as the frequency becomes higher. Also, over the entire frequency region, $\alpha_0$ is smaller and the analysis region is greater for ultra-low-expansion glass #2 than for ultra-low-expansion glass #1. As a result, it can be anticipated that the measurement reproducibility is higher for ultra-low-expansion glass #2 than for ultra-low-expansion glass #1. It follows that the frequency should be lowered in order to improve reproducibility.

Figure 28:
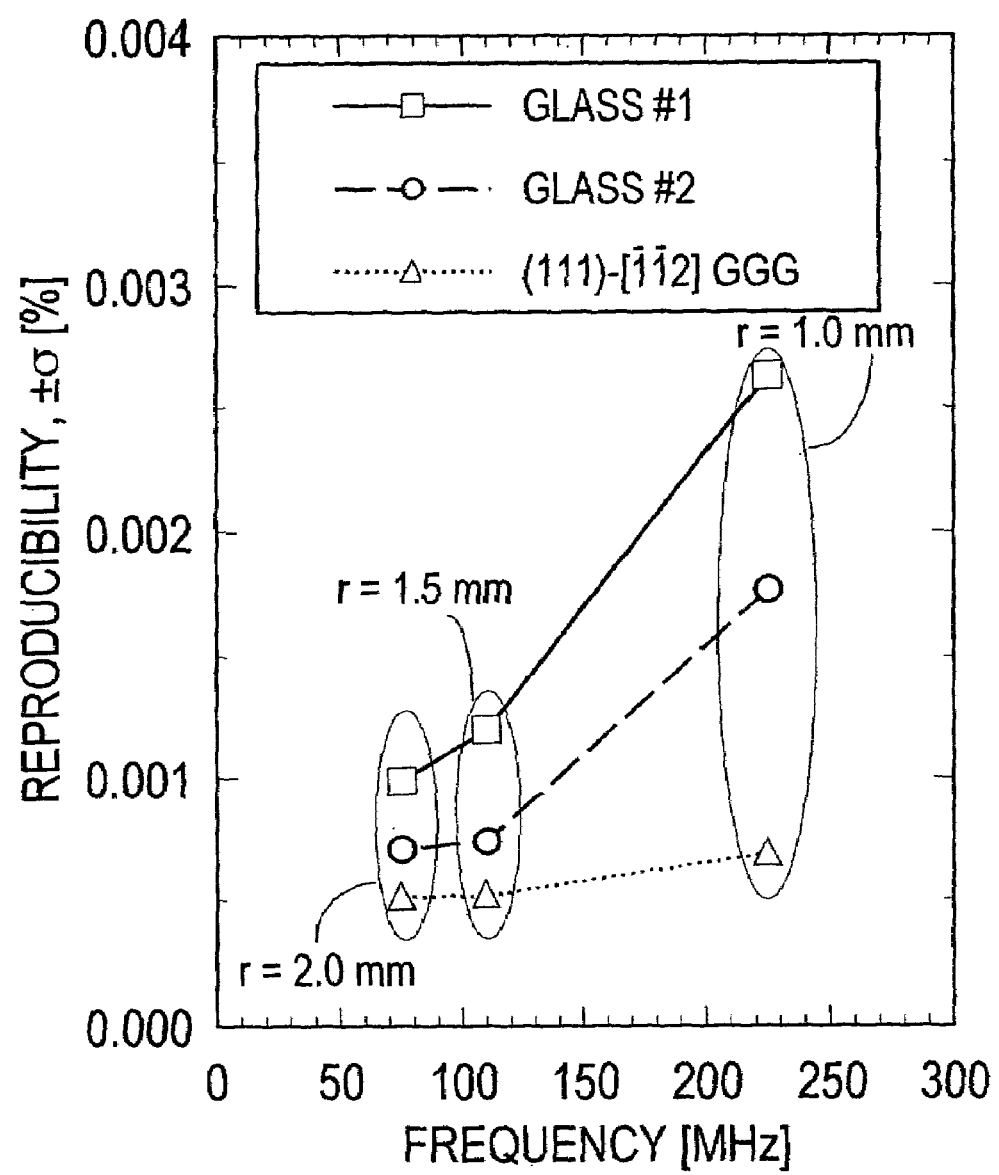
FIG. 28 is a diagram showing the reproducibility of the LSAW velocity with respect to ultra-low-expansion glasses #1 and #2, and (111)-[$\bar{1}\bar{1}2$] GGG.
Figure 29:
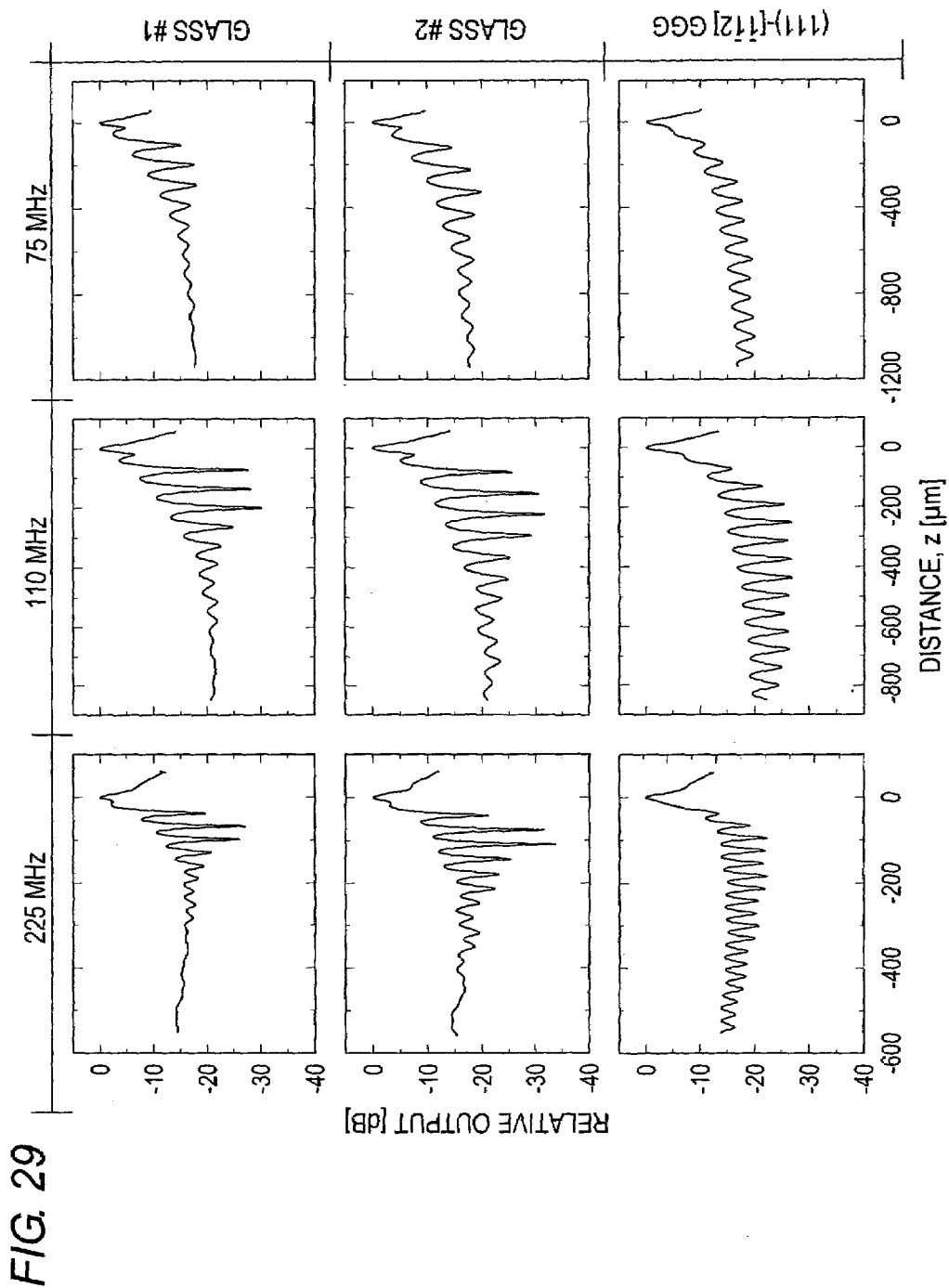
FIG. 29 is a diagram showing the V(z) curves measured by using ultrasonic devices with different parameters, with respect to ultra-low-expansion glasses #1 and #2, and (111)-[$\bar{1}\bar{1}2$] GGG.

Apart from an LFB ultrasonic device (with the curvature radius of the cylindrical lens of r=1.0 mm) for the 200-MHz range normally used in the measurements, two LFB ultrasonic devices having center operating frequencies of 100 MHz (r=1.5 mm) and 70 MHz (r=2.0 mm) were prepared. The maximum defocus distance quantities of the ultrasonic devices are 560 μm, 870 μm, and 1160 μm, respectively. For one frequency selected respectively for these ultrasonic devices, the results of reproducibility (±σ) obtained when repeating the V(z) curve measurements 200 times are shown in FIG. 28. Also, the V(z) curves obtained at this time are shown in FIG. 29. For ultra-low-expansion glass #1, the best reproducibility, ±0.0010%, resulted at 75 MHz. At this point, the resolution for the coefficient of thermal expansion is ±0.14 ppb/K, the resolution for the $TiO_2$ concentration is ±0.0019 wt %, and the resolution for the density is ±0.0006 kg/m$^3$. This value is better than the requirement (±0.2 ppb/K) with respect to evaluation technology for coefficients of thermal expansion, so the present analysis method, which evaluates coefficients of thermal expansion of ultra-low-expansion glass materials by leaky acoustic wave characteristics measured by means of an LFB ultrasonic material characterization system, has been demonstrated to be exceedingly useful as an analytical evaluation method for ultra-low-expansion glasses. Moreover, for the ultra-low-expansion glass #2 and (111) GGG for the [$\bar{1}\bar{1}2$] direction propagation, the reproducibilities are similarly improved to ±0.0007% and ±0.0005%, respectively. However, if the defocus distance quantity for the V(z) curve measurements is increased, the measurement region (the region on which the ultrasonic waves are incident) becomes greater and the spatial resolution in the measurements declines. There is a need to select an appropriate frequency depending on the target of evaluation. As shown in FIG. 19 and FIG. 20, in case glass materials having great changes in their acoustic properties are evaluated, it is sufficient with the 200-MHz range ultrasonic device. However, if application is made to the evaluation of a more homogeneous substrate, measurements should be performed at a lower frequency and evaluation should be performed with a higher measurement accuracy and for the whole substrate.

In order to perform the present analysis method, standard specimens were prepared, and with that process, bulk-wave acoustic velocities were obtained. Although the measurement of bulk wave acoustic velocities takes more time, compared to LSAW velocity measurements, as mentioned above, it is possible to obtain a higher measurement accuracy by diffraction correction taking into account velocity dispersion (Non-Patent Reference 11), an evaluation of the effective radius of the transducer (Non-Patent Reference 12), and a correction of deformation occurring in thickness measurements (Patent Reference 1). In particular, since measurements can be performed for longitudinal waves with water as a coupler, the measurements can be performed comparatively easier. Considering longitudinal velocity errors, the influence of specimen thickness measurement errors and phase measurement errors can be imagined. Since the standard specimen of ultra-low-expansion glass #1 used this time is with a thickness of 4814.14 μm, and the thickness measurement accuracy is ±0.06 μm, the error in velocity due to the thickness is ±12.5 ppm. Also, the error in velocity due to the phase is ±5.2 ppm (±0.03 m/s). Due to these errors, the root mean square error is 13.5 ppm (±0.08 m/s). The maximum error being taken, whether it is due to the thickness or the phase, ±σ works out to ±0.03 m/s, if this error is considered to be about ±3σ. At this point, the longitudinal velocity sensitivities and resolutions for the other physical/chemical properties can be expressed as in FIG. 30. A resolution of ±0.07 ppb/K for the coefficient of thermal expansion is obtained. Moreover, if application is made to a substrate (with a thickness of 6.35 mm) for EUVL use, the root mean square error of the longitudinal velocity is ±0.02 m/s, so the resolution for the coefficient of thermal expansion is further improved.

From the aforementioned results, if the respective measurement accuracies of the LSAW velocity, the LSSCW velocity, and the longitudinal velocity, and the resolutions for other physical/chemical properties, for ultra-low-expansion glass #1, are consolidated, the results are as shown in FIG. 31. By lowering the ultrasonic frequency, it follows that the measurement accuracy (resolution) for the LSAW velocity can be improved. Moreover, regarding the longitudinal velocity, an accuracy higher than the measurement accuracy that had hardly been attained through conventional measurements of average characteristics on 100-mm thick specimens can be implemented for specimens which are only about 5-mm thick. Due to this fact, it is also possible to perform an analysis/evaluation of the coefficient of thermal expansion with a high accuracy by a measurement of the longitudinal velocity, so, at a stage when an improvement in the homogeneity of substrates has been carried out, the method will be very valid as a technique for performing analytical evaluation and quality control of ultra-homogeneous substrates. Similarly, even in the case where shear waves are used, measurement accuracy of the same order is attained.

Figure 32:
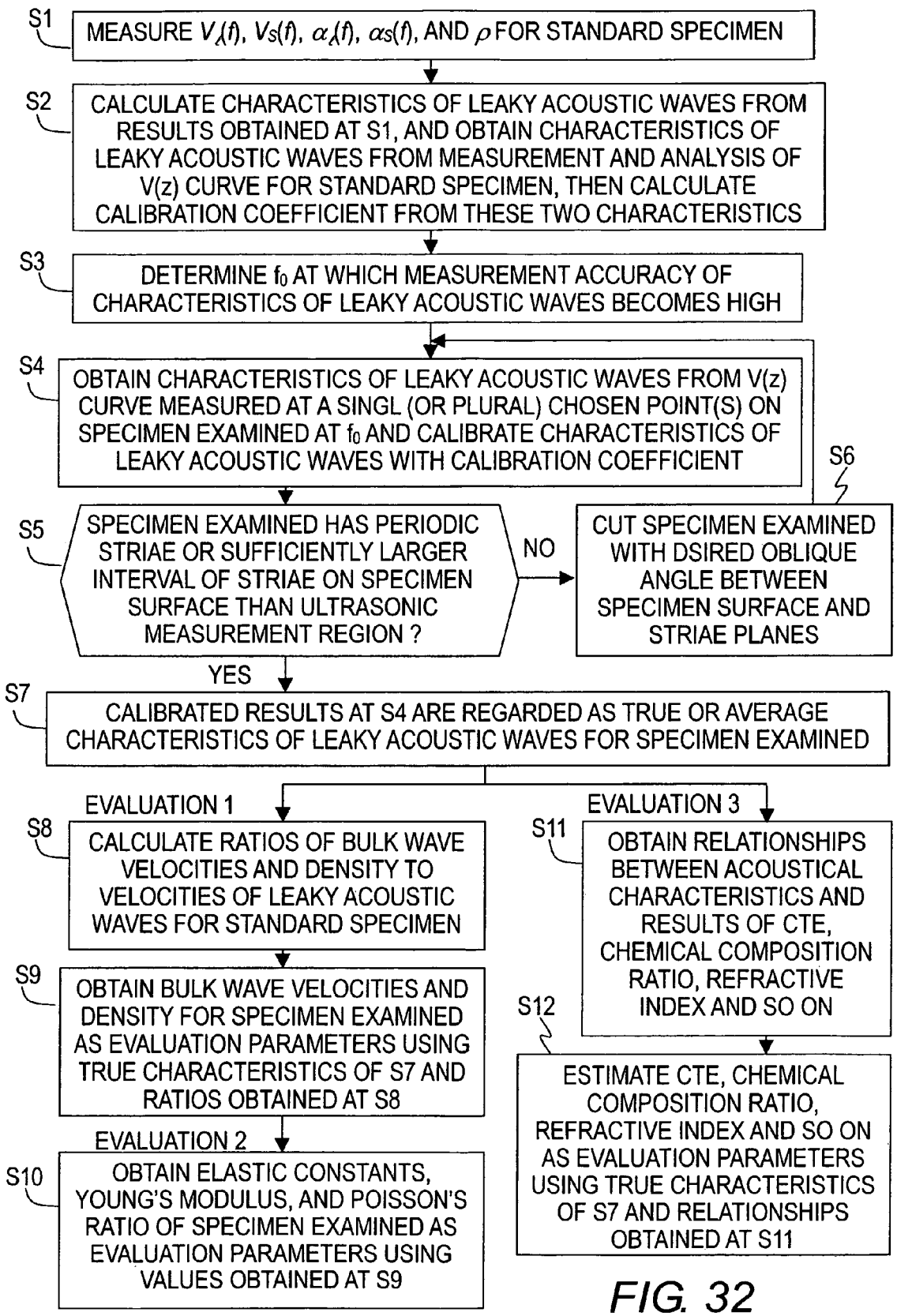
FIG. 32 is a flowchart showing an evaluation procedure, according to this invention, for the coefficient of thermal expansion of ultra-low-expansion glasses.

Based on the embodiment explained above, a fundamental process procedure for the analytical evaluation method for the coefficient of thermal expansion of ultra-low-expansion glasses according to the present invention will be explained with reference to the flowchart of FIG. 32.

Step S1: In the desired temperature and ultrasonic frequency range, the bulk-wave velocities (longitudinal velocity $V_l(f)$ and shear velocity $V_s(f)$), and attenuation coefficients (longitudinal-wave attenuation coefficient $\alpha_l(f)$ and shear-wave attenuation coefficient $\alpha_s(f)$) and the density $\rho$ of a standard specimen are measured.

Step S2: Based on a numerical calculation using the velocities $V_l(f)$ and $V_s(f)$, the attenuation coefficients $\alpha_l(f)$ and $\alpha_s(f)$, and the density $\rho$ obtained in Step S1, there are obtained for the standard specimen the leaky acoustic wave velocities $V_{LSAW}$(std.calc.) and $V_{LSSCW}$(std.calc.) by Eqs. (8) to (15), and the interference intervals $\Delta z_{LSAW}$(std.calc.) and $\Delta z_{LSSCW}$(std.calc.) by Eq. (3), and further, the leaky acoustic wave velocities $V_{LSAW}$(std.meas.) and $V_{LSSCW}$(std.meas.), and the interference intervals $\Delta z_{LSAW}$(std.meas.) and $\Delta z_{LSSCW}$(std.meas.) are obtained from the measured V(z) curve for the standard specimen, and, from the characteristics of these calculated values and measured values for the standard specimen, the calibration coefficients $K_Z$(LSAW) and $K_Z$(LSSCW), or $K_V$(LSAW) and $K_V$(LSSCW) are obtained. The leaky acoustic wave velocities and the interference intervals will together be called the leaky acoustic wave characteristics.

Step S3: Taking into account the normalized propagation attenuation factor of the leaky acoustic wave obtained in Step S2, an ultrasonic frequency $f_0$, for which the measurement accuracy of the leaky acoustic wave characteristics with the used LFB ultrasonic device becomes high, is determined.

Step S4: At the ultrasonic frequency $f_0$ determined in Step S3, a V(z) curve is measured at one or several points on the surface of the measured specimen and the leaky acoustic wave characteristics ($V_{LSAW}$(measured), $V_{LSSCW}$(measured), $\Delta z_{LSAW}$(measured), and $\Delta z_{LSSCW}$(measured)) are obtained, and, with the calibration coefficients obtained in Step S2, calibrated leaky acoustic wave characteristics of the measured specimen are obtained.

Step S5: From the results of Step S4, it is judged whether periodic striae are absent, or whether the periodicity of any striae is sufficiently greater than the ultrasonic measurement region (the region on which the beam is incident).

Step S6: If the judgment result in Step S5 is that, in the measured specimen, periodic striae are present and that the periodicity of the striae is shorter than the ultrasonic measurement region, the surface of the specimen is inclined and cut at a desired angle with respect to the striae plane, and the cut specimen is taken as a substitute measured specimen, for which the leaky acoustic wave characteristic distribution is obtained in Step S4 with the same procedure.

Step S7: In case it was judged in Step S5 that striae are absent, or that the periodicity of the striae is sufficiently greater than the measurement region, the calibrated results obtained in Step S4 are considered as the true (or the average) leaky acoustic wave characteristic distribution for the measured specimen.

First Evaluation

Step S8: The ratio of the shear velocity, obtained by measurement in Step S1, to the LSAW velocity obtained by the calculation in Step S2, the ratio of the longitudinal velocity, obtained by measurement in Step S1, to the LSSCW velocity obtained by the calculation in Step S2, and the ratios of the density to these calculated LSAW and LSSCW velocities are obtained, for the standard specimen.

Step S9: By multiplying the ratios obtained in Step S8 with the calibrated leaky acoustic wave velocities obtained in Step S4, the bulk-wave velocities and the density of the measured specimen are obtained.

Second Evaluation

Step S10: From the values obtained in Step S9, the elastic constants, Young's modulus, and Poisson's ratio obtained with Eqs. (24) to (28) are obtained as evaluation parameters.

Third Evaluation

Step S11: The relationships between the measured results for the coefficient of thermal expansion, the chemical composition ratio, the refractive index, the density, etc., and the calibrated acoustic properties (calibrated leaky acoustic wave velocities, and the bulk-wave velocities, the elastic constants, Young's modulus, etc., estimated on the basis of those velocities) are obtained as evaluation parameters.

Step S12: With respect to the measured results for the acoustic properties and using the relationships obtained in Step S11, the coefficient of thermal expansion, the chemical composition ratio, the refractive index, the density, etc., are considered to be evaluation parameters.

EFFECTS OF THE INVENTION

As mentioned above, according to the present invention, it becomes possible to measure absolute values, even including velocity dispersion characteristics, for both the LSAW and LSSCW propagation modes by measuring the frequency dependence of acoustic velocities and attenuation coefficients as well as the density, for ultra-low-expansion glasses, and it becomes possible to estimate the bulk-wave acoustic properties from a measurement of the V(z) curve by utilizing the relationships between the LSAW and LSSCW velocities and the bulk-wave acoustic properties (longitudinal velocity, shear velocity, density, elastic constants, etc.). By obtaining the relationships between these acoustic properties and the coefficient of thermal expansion, a highly accurate evaluation of the coefficient of thermal expansion based on acoustic property measurements is made possible. Through these results, an evaluation technology can be provided which has the measurement accuracy required for implementing ultra-low-expansion glass materials for EUVL use with an allowable range of ±5 ppb/K for the coefficient of thermal expansion.

INDUSTRIAL APPLICABILITY

An analytical evaluation method for the coefficient of thermal expansion of ultra-low-expansion glasses using leaky acoustic wave velocities measured with an ultrasonic material characterization system can, because it clearly captures the differences of the coefficient of thermal expansion in a glass substrate or between glass substrates, be used not only for glass substrate evaluation, sorting, and quality control, but it can also be used for materials manufacturing process evaluation and improvement. As a result of this, it can contribute to the implementation of ideal glass materials having a zero coefficient of thermal expansion at a desired temperature across an entire ingot. Moreover, the present technique is useful not only for ultra-low-expansion glass materials and, it goes without saying, for synthetic silica glass or ordinary glass or ceramics, but it can also be applied to single crystal materials. Because of this, it is exceedingly useful universally for materials development and evaluation/sorting, and for the improvement of manufacturing processes, and so forth.

What is claimed is:

1. An evaluation method for a coefficient of thermal expansion of an ultra-low-expansion glass material, including:

(a) a step of measuring, in the used ultrasonic frequency range, the longitudinal velocity and attenuation coefficient, the shear velocity and attenuation coefficient, and the density, of a standard specimen of the ultra-low-expansion glass material;
(b) a step of calculating a first leaky acoustic wave characteristic with respect to said standard specimen, from said acoustic velocities, attenuation coefficients, and density;
(c) a step of obtaining, by measuring the leaky acoustic wave interference signal curve V(z) with respect to said standard specimen, a second leaky acoustic wave characteristic from that V(z) curve;
(d) a step of obtaining, as a calibration coefficient, the ratio of said first leaky acoustic wave characteristic calculated in said Step (b) and said second leaky acoustic wave characteristic obtained from said V(z) curve in Step (c);
(e) a step of measuring a V(z) curve with respect to the measured specimen of the ultra-low-expansion glass material and obtaining from that V(z) curve a third leaky acoustic wave characteristic;
(f) a step of calibrating, with said calibration coefficient, said third leaky acoustic wave characteristic obtained for said measured specimen;
(g) a step of obtaining the relationship between the coefficient of thermal expansion of said ultra-low-expansion glass material and said third leaky acoustic wave characteristic, absolutely calibrated; and
(h) a step of measuring a fourth leaky acoustic wave characteristic with respect to the ultra-low-expansion glass specimen under evaluation, and, based on said relationship, evaluating the coefficient of thermal expansion.

2. The evaluation method according to claim 1, wherein:
said step (b) includes a step of calculating the leaky surface acoustic wave velocity $V_{LSAW}$(std.calc.) of said standard specimen from said acoustic velocities, attenuation coefficients, and density, and, from the calculated results, calculating an interference interval $\Delta z_{LSAW}$(std.calc.) of the leaky surface acoustic wave of the corresponding V(z) curve as one of said leaky acoustic wave characteristics;
said step (c) includes obtaining an interference interval $\Delta z_{LSAW}$(std.meas.) of the leaky surface acoustic wave from said V(z) curve regarding said standard specimen;
said step (d) includes obtaining a ratio $K_Z(LSAW)=\Delta z_{LSAW}$(std.calc.)$/\Delta z_{LSAW}$(std.meas.) of the interference intervals of said leaky surface acoustic wave as said calibration coefficient;
said step (e) includes obtaining the interference interval $\Delta z_{LSAW}$(measured) of the leaky surface acoustic wave from the V(z) curve regarding said measured specimen as one of said leaky acoustic wave characteristics; and
said step (f) includes obtaining an interference interval $\Delta z_{LSAW}$(calibrated)=$K_Z$(LSAW)$\Delta z_{LSAW}$(measured), calibrated with said calibration coefficient $K_Z$(LSAW) from the interference interval $\Delta z_{LSAW}$(measured) of said measured specimen, and obtaining, by calculation, from the calibrated interference interval $\Delta z_{LSAW}$(calibrated), the calibrated leaky surface acoustic wave velocity $V_{LSAW}$(calibrated) of said measured specimen as said calibrated leaky acoustic wave characteristic.

3. The evaluation method according to claim 1, wherein:
said step (b) further includes a step of calculating the leaky surface-skimming compressional wave velocity $V_{LSSCW}$(std.calc.) of said standard specimen from said acoustic velocities, attenuation coefficients, and density, and, from the calculated results, calculating an interference interval $\Delta z_{LSSCW}$(std.calc.) of the leaky surface-skimming compressional wave of the corresponding V(z) curve as one of said leaky acoustic wave characteristics;
said step (c) further includes obtaining an interference interval $\Delta z_{LSSCW}$(std.meas.) of the leaky surface-skimming compressional wave from said V(z) curve regarding said standard specimen;
said step (d) further includes obtaining a ratio $K_Z(LSSCW)=\Delta z_{LSSCW}$(std.calc.)$/\Delta z_{LSSCW}$(std.meas.) of the interference intervals of said leaky surface-skimming compressional wave as said calibration coefficient;
said step (e) further includes obtaining the interference interval $\Delta z_{LSSCW}$(measured) of the leaky surface-skimming compressional wave from the V(z) curve regarding said measured specimen as one of said leaky acoustic wave characteristics; and
said step (f) further includes obtaining an interference interval $\Delta z_{LSSCW}$(calibrated)=$K_Z$(LSSCW)$\Delta z_{LSSCW}$(measured), calibrated with said calibration coefficient $K_Z$(LSSCW) from the interference interval $\Delta z_{LSSCW}$(measured) of said measured specimen, and obtaining by calculation, from the calibrated interference interval $\Delta z_{LSSCW}$(calibrated), the calibrated leaky surface-skimming compressional wave velocity $V_{LSSCW}$(calibrated) of said measured specimen as said calibrated leaky acoustic wave characteristic.

4. The evaluation method according to claim 1, wherein:
said step (b) includes a step of calculating the leaky surface acoustic wave velocity $V_{LSAW}$(std.calc.) of said standard specimen from said acoustic velocities, attenuation coefficients, and density, as one of said leaky acoustic wave characteristics;
said step (c) includes obtaining a velocity $V_{LSAW}$(std.meas.) of the leaky surface acoustic wave from said V(z) curve regarding said standard specimen;
said step (d) includes obtaining a ratio $K_V(LSAW)=V_{LSAW}$(std.calc.)$/V_{LSAW}$(std.meas.) of the velocities of said leaky surface acoustic wave as said calibration coefficient;
said step (e) includes obtaining the leaky surface acoustic wave velocity $V_{LSAW}$(measured) from the V(z) curve regarding said measured specimen as one of said leaky acoustic wave characteristics; and
said step (f) includes obtaining a leaky surface acoustic wave velocity $V_{LSAW}$(calibrated)=$K_V$(LSAW)$V_{LSAW}$(measured), calibrated with said calibration coefficient $K_V$(LSAW) from the leaky surface acoustic wave velocity $V_{LSAW}$(measured) of said measured specimen, and obtaining, by calculation, the calibrated leaky surface acoustic wave velocity $V_{LSAW}$(calibrated) of said measured specimen as said calibrated leaky acoustic wave characteristic.

5. The evaluation method according to claim 1, wherein:
said step (b) further includes a step of calculating the leaky surface-skimming compressional wave velocity $V_{LSSCW}$(std.calc.) of said standard specimen from said acoustic velocities, attenuation coefficients, and density, as one of said leaky acoustic wave characteristics;
said step (c) further includes obtaining a velocity $V_{LSSCW}$(std.meas.) of the leaky surface-skimming compressional wave from said V(z) curve regarding said standard specimen;

said step (d) further includes obtaining a ratio $K_V(LSSCW)=V_{LSSCW}(std.calc.)/V_{LSSCW}(std.meas.)$ of the velocities of said leaky surface-skimming compressional wave as said calibration coefficient;

said step (e) further includes obtaining the leaky surface-skimming compressional wave velocity $V_{LSSCW}$(measured) from the V(z) curve regarding said measured specimen as one of said leaky acoustic wave characteristics; and said step (f) further includes obtaining a leaky surface-skimming compressional wave velocity $V_{LSSCW}$(calibrated)=$K_V(LSSCW)V_{LSSCW}$(measured), calibrated with said calibration coefficient $K_V(LSSCW)$ from the leaky surface-skimming compressional wave velocity $V_{LSSCW}$ (measured) of said measured specimen, and obtaining, by calculation, the calibrated leaky surface-skimming compressional wave velocity $V_{LSSCW}$ (calibrated) of said measured specimen as said calibrated leaky acoustic wave characteristic.

6. The evaluation method according to claim 1, wherein:

said Step (g), in case periodic striae are present in said ultra-low-expansion glass specimen under evaluation, includes a step of cutting out a specimen inclined at a desired angle with respect to the striae plane and taking it as a substitute specimen.

7. The evaluation method according to claim 1, wherein:

said Step (g), in case the propagation attenuation of the leaky acoustic wave of said specimen under evaluation is high, measures the leaky acoustic wave characteristics by using a lower ultrasonic frequency.

* * * * *